(12) United States Patent
Miyoshi et al.

(10) Patent No.: US 7,947,504 B2
(45) Date of Patent: May 24, 2011

(54) TUMOR MARKER FOR PANCREATIC CANCER AND METHOD OF TESTING THE SAME

(75) Inventors: Eiji Miyoshi, Toyonaka (JP); Naoyuki Taniguchi, Toyonaka (JP); Miyako Nakano, Kawachinagano (JP)

(73) Assignee: Wako Pure Chemical Industries Ltd., Osaka-shi (JP)

( * ) Notice: Subject to any disclaimer, the term of this patent is extended or adjusted under 35 U.S.C. 154(b) by 393 days.

(21) Appl. No.: 12/155,041

(22) Filed: May 29, 2008

(65) Prior Publication Data

US 2009/0181461 A1    Jul. 16, 2009

(30) Foreign Application Priority Data

Jan. 10, 2008   (JP) ................. 2008-003696

(51) Int. Cl.
*G01N 33/48* (2006.01)
(52) U.S. Cl. ............... 436/64; 436/63; 436/86; 436/87; 436/89; 436/94
(58) Field of Classification Search .............. 436/63, 436/64, 86, 87, 89, 94
See application file for complete search history.

(56) References Cited

U.S. PATENT DOCUMENTS

| | | | |
|---|---|---|---|
| 2006/0269974 A1* | 11/2006 | Dwek et al. | 435/7.23 |
| 2007/0059783 A1* | 3/2007 | Packer et al. | 435/7.23 |
| 2007/0178538 A1* | 8/2007 | Haab | 435/7.23 |
| 2009/0136960 A1* | 5/2009 | Lubman et al. | 435/6 |

OTHER PUBLICATIONS

Zhao et al. Journal of Proteome Research, vol. 6, Apr. 12, 2007, pp. 1864-1874.*
Nakano et al. International Journal of Cancer, vol. 122, Jan. 23, 2008, pp. 2301-2309.*
"Fucosylated Haptoglobin in a Novel Marker for Pancreatic Cancer: A Detailed Analysis of the Oligosaccharide Structure and a Possible Mechanism for Fucosylation," Int. J. Cancer: 118, pp. 2803-2808 (2006), 2005 Wiley-Liss, Inc., Publication of the International Union Against Cancer.

* cited by examiner

*Primary Examiner* — Maureen M Wallenhorst
(74) *Attorney, Agent, or Firm* — Edwards Angell Palmer & Dodge LLP

(57) ABSTRACT

The determination (test, diagnosis) of pancreatic cancer can be performed with high accuracy by detecting a fucosylated sugar chain (N-glycan) present in a specific site of the human haptoglobin and using an amount of the fucosylated sugar chain as a tumor marker for pancreatic cancer.

9 Claims, 5 Drawing Sheets

TUMOR MARKER FOR PANCREATIC CANCER AND METHOD OF TESTING THE SAME

BACKGROUND OF THE INVENTION

The present invention relates to a tumor marker for pancreatic cancer and a method for determining (diagnosing/testing) pancreatic cancer.

Pancreatic cancer is a typical intractable cancer, and the prime reason for the obstinacy is difficulty in early diagnosis.

Currently, as tumor markers (diagnostic markers) for pancreatic cancer, CEA, CA19-9, CA-50, elastase 1, Span-1, DUPAN-2 and the like have been developed and used in clinical diagnosis. However, since there remains some problems that these tumor markers are detected as positive not only in pancreatic cancer, but also in benign hepatic disorders such as chronic hepatitis and hepatic cirrhosis as well as in chronic pancreatitis, and in tumors other than pancreatic cancer (e.g. stomach cancer, colon cancer), or detected as negative in a particular pancreatic cancer, these markers are not satisfiable with respect to the specificity and accuracy in detecting and diagnosing pancreatic cancer.

On the other hand, haptoglobin is a glycoprotein having specific affinity for hemoglobin. The human haptoglobin is a tetramer composed of 2 subunits (α- and β-) with molecular weight of about 90 KD, and classified into 3 types including haptoglobin 1-1 (Hp1-1), haptoglobin 2-1 (Hp2-1) and haptoglobin 2-2 (Hp2-2).

In recent years, the relationship between fucosylated haptoglobin and various types of cancers has been studied, and it has been pointed out that the fucosylated haptoglobin may be useful for the detection of pancreatic cancer (non-patent reference 1: Okuyama N, et al., Int J Cancer. Jun. 1, 2006; 118(11):2803-8).

BRIEF SUMMARY OF THE INVENTION

An object of the present invention is to provide a novel tumor marker (a tumor marker for pancreatic cancer) and a method of determining pancreatic cancer with high specificity using the same.

The tumor marker for pancreatic cancer of the present invention is a novel tumor marker and useful for detecting pancreatic cancer, and also, the determination method of the present invention is capable of determining (diagnosing, testing) pancreatic cancer with high accuracy.

The present invention has been made for the purpose of achieving the above-described object, and comprises the following aspects:

(1) A method of determining pancreatic cancer, comprising detecting a fucosylated sugar chain bound to asparagine at the 184th and/or the 211th from N-terminal of amino acid sequence of the human haptoglobin;

(2) A tumor marker for pancreatic cancer, comprising a carbohydrate structure (sequence) present in the human haptoglobin and shown by the following structural formula [III], wherein at least one of N-acetylglucosamine (GlcNAc) in tetraantennary sugar chain present in non-reducing terminal side is fucosylated;

[III]

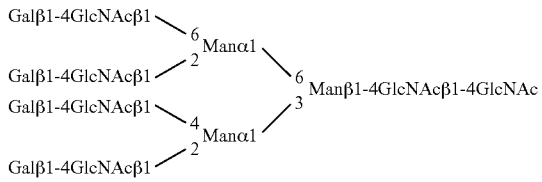

(3) A method of determining pancreatic cancer, comprising detecting the tumor marker for pancreatic cancer according to the above item (2) present in a biological sample.

BPC in FIG. 3A is the BPC obtained in Example 1 on the human haptoglobin derived from the serum of normal volunteer (NV5), which has been digested by trypsin and lysylendopeptidase.

EIC of MSMS (at m/z 657.3) in FIG. 3A is a chromatogram obtained in Example 1 showing peak intensity of the fragment ion having a mass number of 657.3 m/z generated by MSMS measurement of the human haptoglobin derived from the serum of normal volunteer (NV5), which has been digested by trypsin and lysylendopeptidase.

EIC of MS (at 1221.8-1222.8 m/z) Site 1 in FIG. 3A is a chromatogram obtained in Example 1 showing peak intensities of the fragment ions having mass numbers of 1221.8-1222.8 m/z generated by MS measurement of the human haptoglobin derived from the serum of normal volunteer (NV5), which has been digested by trypsin and lysylendopeptidase.

EIC of MS (at 1467.8-1468.8 m/z) Site 2-3 in FIG. 3A is a chromatogram obtained in Example 1 showing peak intensities of the fragment ions having mass numbers of 1467.8-1468.8 m/z generated by MS measurement of the human haptoglobin derived from the serum of a normal volunteer (NV5), which has been digested by trypsin and lysylendopeptidase.

EIC of MS (at 1333.9-1334.9 m/z) Site 4 in FIG. 3A is a chromatogram obtained in Example 1 showing peak intensities of the fragment ions having mass numbers of 1333.9-1334.9 m/z generated by MS measurement of the human haptoglobin derived from the serum of a normal volunteer (NV5), which has been digested by trypsin and lysylendopeptidase.

NV5 Site 1 in FIG. 3B is the results, obtained in Example 1, of the averaging of the mass spectra near the elution positions (67-72 minutes) of glycopeptides containing Site 1, identified in the human haptoglobin derived from the serum of a normal volunteer (NV5), which has been digested by trypsin and lysylendopeptidase.

CP4 Site 1 in FIG. 3B is the results, obtained in Example 1, of the averaging of the mass spectra near the elution positions (67-72 minutes) of glycopeptides containing Site 1, identified in the human haptoglobin derived from the serum of a patient with chronic pancreatitis (CP4), which has been digested by trypsin and lysylendopeptidase.

PC5 Site 1 in FIG. 3B is the results, obtained in Example 1, of the averaging of the mass spectra near the elution positions (67-72 minutes) of glycopeptides containing Site 1, identified in the human haptoglobin derived from the serum of a patient with pancreatic cancer (PC5), which has been digested by trypsin and lysylendopeptidase.

Figure 4:
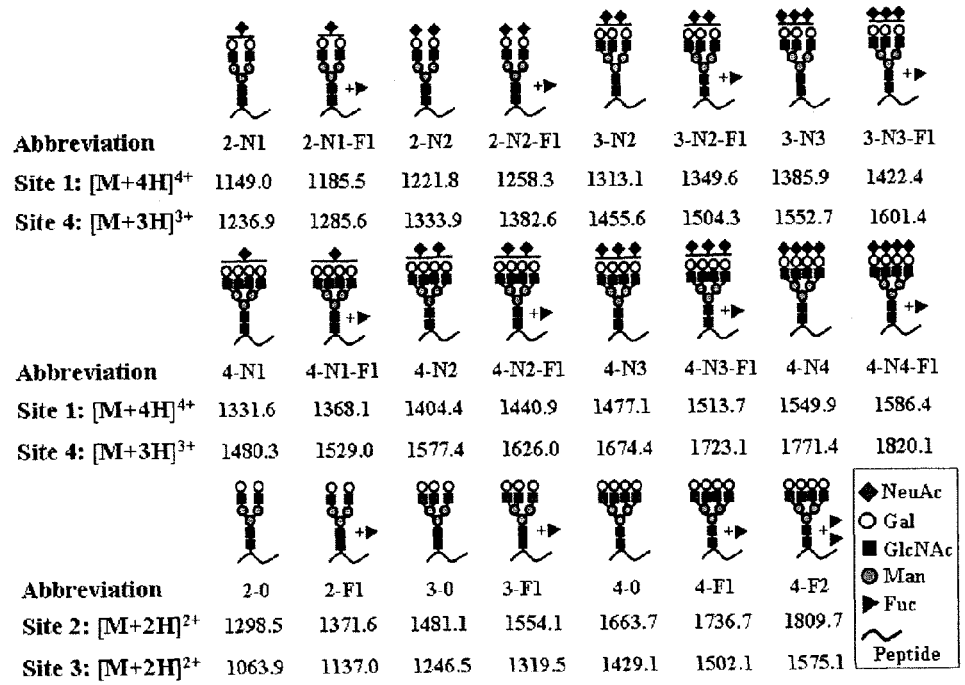

FIG. 4 shows a relationship between peptide fragments having various types of carbohydrate structures (glycopeptides) in each Site and the mass numbers thereof.

Figure 5:
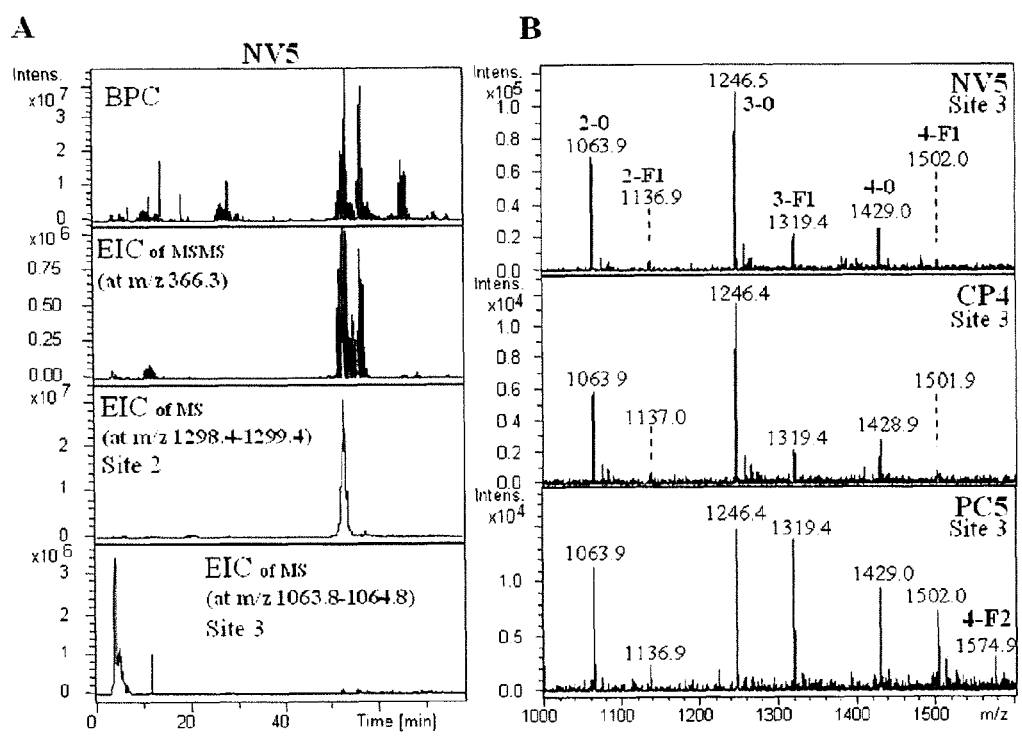

FIG. 5 shows the followings:

BPC in FIG. 5A is the BPC, obtained in Example 1, of the human haptoglobin derived from the serum of normal volunteer (NV5), which has been digested by trypsin, lysylendopeptidase and endopeptidase Glu-C and treated with acid (desialylated).

EIC of MSMS (at m/z 366.3) in FIG. 5A is a chromatogram, obtained in Example 1, showing peak intensity of the fragment ion having a mass number of 366.3 m/z generated by MSMS measurement of the human haptoglobin derived from the serum of normal volunteer (NV5), which has been digested by trypsin, lysylendopeptidase and endopeptidase Glu-C and treated with acid (desialylated).

EIC of MS (at 1298.4-1299.4 m/z) Site 2 in FIG. 5A is a chromatogram, obtained in Example 1, showing peak intensities of the fragment ions having mass numbers of 1298.4-1299.4 m/z generated by MS measurement of the human haptoglobin derived from the serum of normal volunteer (NV5), which has been digested by trypsin, lysylendopeptidase and endopeptidase Glu-C and treated with acid (desialylated).

EIC of MS (at 1063.8-1064.8 m/z) Site 3 in FIG. 5A is a chromatogram, obtained in Example 1, showing peak intensities of the fragment ions having mass numbers of 1063.8-1064.8 m/z generated by MS measurement of the human haptoglobin derived from the serum of normal volunteer (NV5), which has been digested by trypsin, lysylendopeptidase and endopeptidase Glu-C and treated with acid (desialylated).

NV5 Site 3 in FIG. 5B is the results, obtained in Example 1, of the averaging of the mass spectra near the elution positions (3-8 minutes) of glycopeptides containing Site 3, identified in the human haptoglobin derived from the serum of a normal volunteer (NV5), which has been digested by trypsin, lysylendopeptidase and endopeptidase Glu-C and treated with acid (desialylated).

CP4 Site 3 in FIG. 5B is the results, obtained in Example 1, of the averaging of the mass spectra near the elution positions (3-8 minutes) of glycopeptides containing Site 3, identified in the human haptoglobin derived from the serum of a patient with chronic pancreatitis (CP4), which has been digested by trypsin, lysylendopeptidase and endopeptidase Glu-C and treated with acid (desialylated).

PC5 Site 3 in FIG. 5B is the results, obtained in Example 1, of the averaging of the mass spectra near the elution positions (3-8 minutes) of glycopeptides containing Site 3, identified in the human haptoglobin derived from the serum of a patient with pancreatic cancer (PC5), which has been digested by trypsin, lysylendopeptidase and endopeptidase Glu-C and treated with acid (desialylated).

Figure 6:
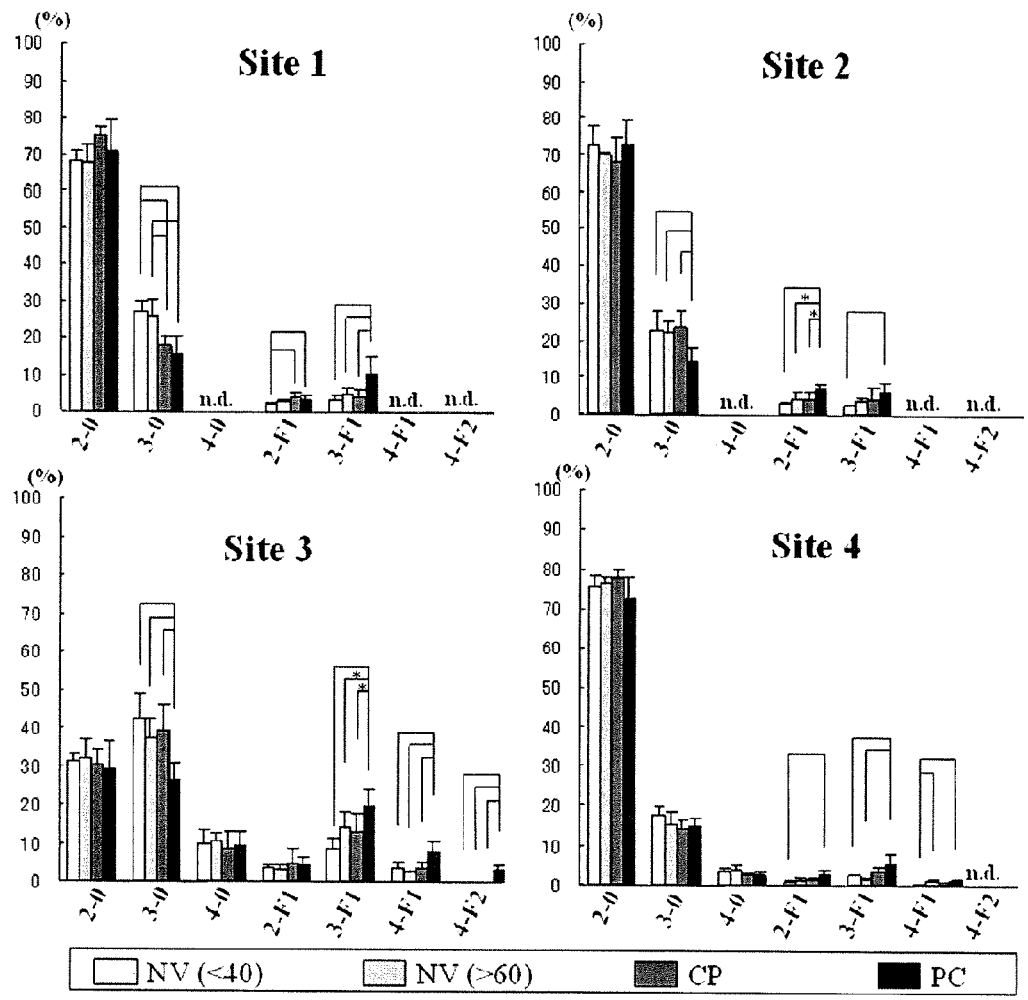

FIG. 6 shows a relationship, obtained in Example 1, between the relative abundance of sugar chain with asialo-structure in each Site and each test sample.

Figure 7:
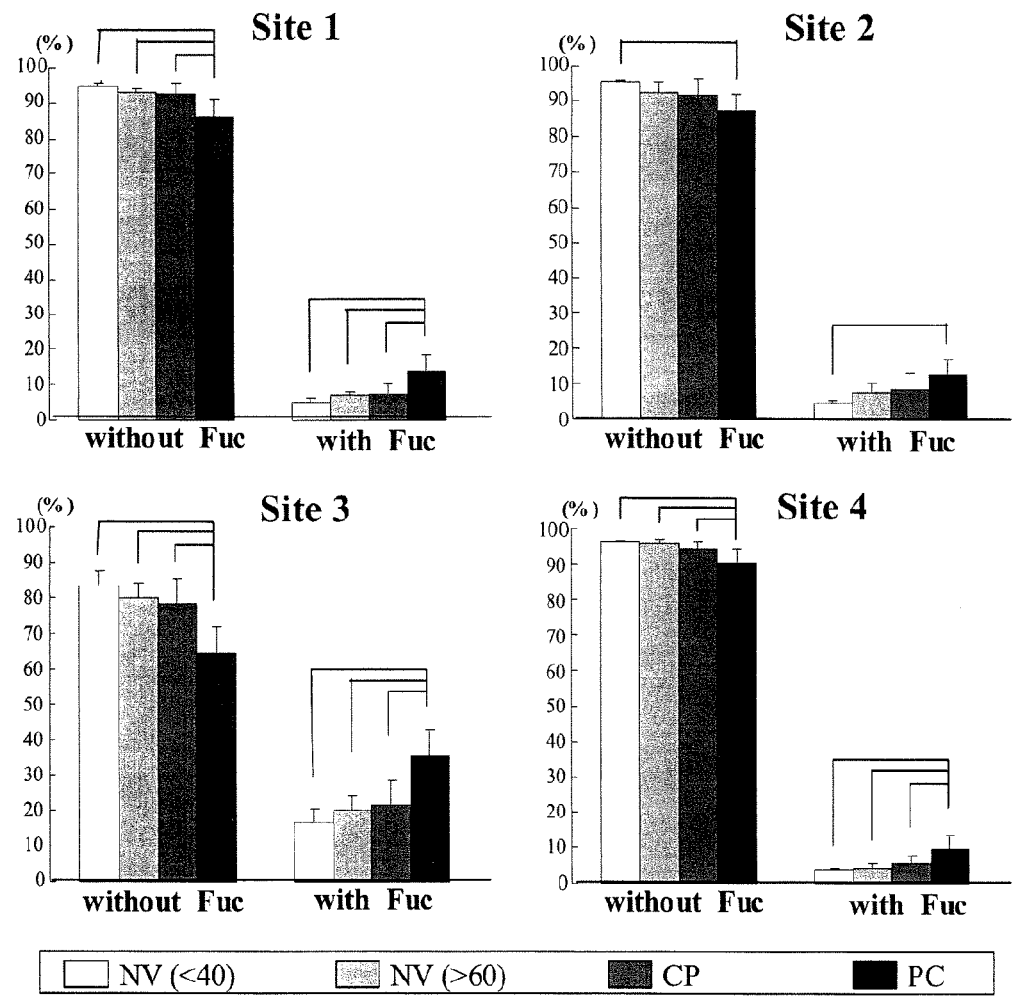

FIG. 7 shows a relationship, obtained in Example 1, between both the relative abundance of fucosylated sugar chain and the relative abundance of unfucosylated sugar chain in each Site and each test sample.

DETAILED DESCRIPTION OF THE INVENTION

The present inventors have intensively studied to achieve the above-described purpose, and analyzed in detail the relationship between pancreatic cancer and the fucosylated sugar chain present in the human haptoglobins. As the result, the present inventors have found that a level of the fucosylated sugar chain (N-glycan) present in a specific site of the human haptoglobin in a test sample from patients with pancreatic cancer is increased significantly as compared with that in a test sample from normal volunteers and patients with chronic pancreatitis, and degree of augmentation is significantly greater than that of the fucosylated sugar chain present in the sites other than the aforementioned specific site, and also that if the fucosylated sugar chain present in the aforementioned specific site is used as an indicator, that is, as a tumor marker for pancreatic cancer, determination (test, diagnosis) of pancreatic cancer can be performed with high accuracy, and have thus completed the present invention.

1. A Tumor Marker for Pancreatic Cancer of the Present Invention:

A tumor marker for pancreatic cancer of the present invention is a fucosylated sugar chain (N-glycan) bound to asparagine at the $184^{th}$ (Site 1) and/or a fucosylated sugar chain (N-glycan) bound to asparagine at the $211^{th}$ (Site 3) from N-terminal (methionine terminal) in the amino acid sequence of the human haptoglobin.

The human haptoglobin has four sugar-chain binding sites, Site 1 to Site 4, in its β-subunit;

(a) Site 1: asparagine at the $184^{th}$ from N-terminal (methionine terminal);

(b) Site 2: asparagine at the $207^{th}$ from N-terminal (methionine terminal);

(c) Site 3: asparagine at the $211^{th}$ from N-terminal (methionine terminal); and (d) Site 4: asparagine at the $241^{st}$ from N-terminal (methionine terminal).

Figure 1:
FIG. 1 shows the positions of the Site 1 to 4 in the amino acid sequence of human haptoglobin.

The positions of the Site 1 to 4 in the amino acid sequence of the human haptoglobin are shown in FIG. 1.

As shown in Examples described hereinafter, samples from a patient with pancreatic cancer, a patient with chronic pancreatitis and a normal volunteer were compared, and it was found that, among these four binding sites, the fucosylated sugar chain binding to the Site 1 and the fucosylated sugar chain binding to the Site 3 showed higher significant difference for pancreatic cancer compared with that of the fucosylated sugar chain binding to the Site 2 and the fucosylated sugar chain binding to the Site 4, indicating usefulness of the fucosylated sugar chain as a tumor marker for pancreatic cancer.

The tumor marker for pancreatic cancer of the present invention is specifically the fucosylated sugar chain comprising a carbohydrate structure (sequence) shown by the following structural formulas [I] to [III], and any one of sugar residues in the aforementioned sugar chains is fucosylated (Fuc) (hereinafter, may be abbreviated as tumor marker for pancreatic cancer [I], [II] or [III]).

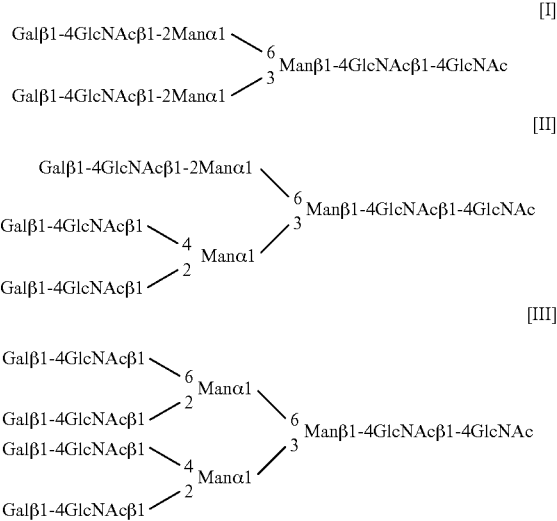

More specifically, the tumor marker for pancreatic cancer includes, (1) a fucosylated sugar chain comprising the carbohydrate structure (sequence) shown by the above-described structural formula [I], in which N-acetylglucosamine (GlcNAc) present in the reducing terminal side (root of the sugar chain) is fucosylated; (2) a fucosylated sugar chain comprising the carbohydrate structure (sequence) shown by the above-described structural formula [III], in which any one of N-acetylglucosamine (GlcNAc) in a triantennary sugar chain present in the non-reducing terminal side (head of the sugar chain) is fucosylated; (3) a fucosylated sugar chain comprising the carbohydrate structure (sequence) shown by the above described structural formulas [III], in which any one of N-acetylglucosamine (GlcNAc) in a tetraantennary sugar chain present in the non-reducing terminal side is fucosylated; and (4) a fucosylated sugar chain comprising the carbohydrate structure (sequence) shown by the above-described structural formula [III], in which at least 2 residues including any one of N-acetylglucosamine (GlcNAc) in a tetraantennary sugar chain present in the non-reducing terminal side and any one of galactose (Gal) in a tetraantennary sugar chain present in the non-reducing terminal side are fucosylated, and the like. Among them, (3) a fucosylated sugar chain comprising the carbohydrate structure (sequence) shown by the above described structural formula [III], in which any one of N-acetylglucosamine (GlcNAc) in a tetraantennary sugar chain present in the non-reducing-terminal side is fucosylated and (4) a fucosylated sugar chain comprising the carbohydrate structure (sequence) shown by the above described structural formula [III], in which at least 2 residues including any one of N-acetylglucosamine (GlcNAc) in a tetraantennary sugar chain present in the non-reducing-terminal side and any one of galactose (Gal) in a tetraantennary sugar chain present in the non-reducing-terminal side are fucosylated are preferable.

The fucosylated sugar chain comprising the carbohydrate structure (sequence) shown by the structural formulas [I] to [III] may be the one which comprises the aforementioned carbohydrate structure in which any of sites are fucosylated, including, for example, the one in which the galactose (Gal) at non-reducing terminal of the above-mentioned carbohydrate structure is not coupled with sialic acid (N-acetyl-neuraminic acid: NeuAc) (asialo-form) (the one comprised only of these carbohydrate structure), and the one in which one or more of the plural number of galactose (Gal) at non-reducing-terminal are coupled with sialic acid (NeuAc) (sialo-form).

That is, the tumor marker for pancreatic cancer [I] of the present invention encompasses the one which is comprised only of the structure shown by the above described structural formula [I] (asialo-form), the one in which any one of 2 galactoses (Gal) at non-reducing terminal in the above-described structural formula [I] is coupled with sialic acid (NeuAc) (monosialo-form), and the one in which all of the 2 galactoses (Gal) are coupled with sialic acid (NeuAc) (disialo-form). In addition, the tumor marker for pancreatic cancer [II] of the present invention encompasses the one which is comprised only of the structure shown by the above described structural formula [II] (asialo-form), the one in which any one of 3 galactoses (Gal) at non-reducing terminal in the above-described structural formula [II] is coupled with sialic acid (NeuAc) (monosialo-form), the one in which any 2 of the 3 galactoses (Gal) are coupled with sialic acid (NeuAc) (disialo-form), and the one in which all of the 3 galactoses (Gal) are coupled with sialic acid (NeuAc) (trisialo-form). In addition, the tumor marker for pancreatic cancer [III] of the present invention encompasses the one which is comprised only of the structure shown by the above described structural formula [III] (asialo-form), the one in which any one of 4 galactoses (Gal) at non-reducing terminal in the above described structural formula [III] is coupled with sialic acid (NeuAc) (monosialo-form), the one in which any 2 of the 4 galactoses (Gal) are coupled with sialic acid (NeuAc) (disialo-form), the one in which any 3 of the 4 galactoses (Gal) are coupled with sialic acid (NeuAc) (trisialo-form), and the one in which all of the 4 galactoses (Gal) are coupled with sialic acid (NeuAc) (tetrasialo-form).

In more specifically, the fucosylated sugar chains comprising the carbohydrate structures (sequences) shown by the following structural formulas [1] to [4] (hereinafter, may be abbreviated as a tumor marker for pancreatic cancer [1], [2], [3] or [4]) are preferable. It should be noted that the fucosylated sugar chains comprising the carbohydrate structures (sequences) shown by the following structural formulas [1] to [4] may be the one which comprises the aforementioned carbohydrate structure, including, for example, the one in which the galactose (Gal) at non-reducing terminal of the carbohydrate structure mentioned below is not coupled with sialic acid (N-acetylneuraminic acid: NeuAc) (asialo-form) (the one comprised only of these carbohydrate structures), and the one in which one or more of the plural number of galactose (Gal) at non-reducing terminal are coupled with sialic acid (NeuAc) (sialo-form). (It should be noted that the binding relationship between plural number of galactose (Gal) at non-reducing terminal and sialic acid is the same as described in the tumor marker for pancreatic cancer [I]-[III].)

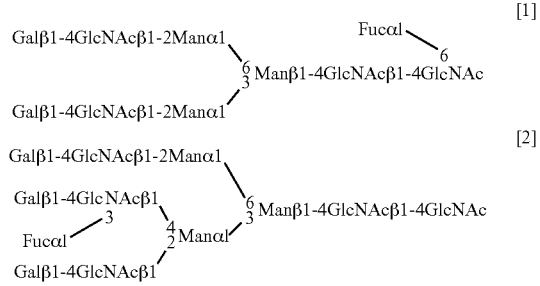

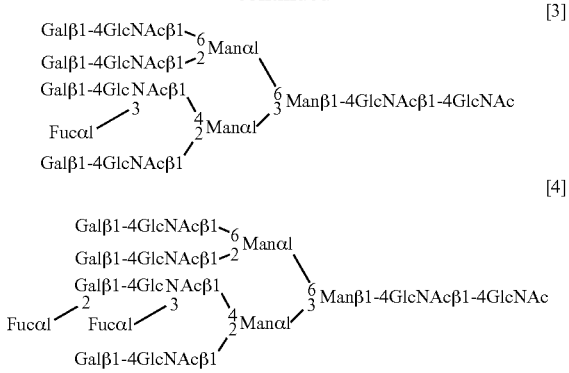

[3]

[4]

Among them, as shown in Examples described later, the tumor markers for pancreatic cancer [3] and [4] of the present invention are present in the Site 3, but almost never in the other Sites. Especially, the tumor marker for pancreatic cancer [4] of the present invention is present in the test sample from patients with pancreatic cancer, but almost never present in the test sample from patients with chronic pancreatitis and normal volunteers, and is, therefore, distinctly useful as a tumor marker for pancreatic cancer.

2. The Method of Determining Pancreatic Cancer of the Present Invention:

The method of determining pancreatic cancer of the present invention is characterized in that the fucosylated sugar chain (N-glycan) bound to the above-described Site 1 and/or the Site 3, which is present in a biological sample, is detected.

That is, in the method of determining pancreatic cancer of the present invention, an amount of the fucosylated sugar chain (N-glycan) bound to the above-described Site 1 and/or the Site 3 is used as a marker (or an indicator) for the determination (diagnosis, test).

In the present invention, an amount of the fucosylated sugar chain in the Site 1 only may be used as a marker (or an indicator), or an amount of the fucosylated sugar chain in the Site 3 only may be used as a marker (or an indicator), and further the total amount of the fucosylated sugar chain in both of the Site 1 and the Site 3 may be used as a marker (or an indicator).

In addition, the fucosylated sugar chain to be used as a marker (or an indicator) may be either the total amount of the tumor markers for pancreatic cancer of the present invention [I], [II] and [III], or an amount of any one or two types of [I], [II] and [III].

Specifically, the fucosylated sugar chain to be used as a marker (or an indicator) is the total amount of the tumor markers for pancreatic cancer of the present invention [1], [2], [3] and [4], or an amount of any one to three types of the tumor markers for pancreatic cancer of the present invention [1], [2], [3] and [4].

Particularly, when an amount of the fucosylated sugar chain in the Site 1 is used as a marker (or an indicator), an amount of the tumor marker for pancreatic cancer of the present invention [II] is preferably used as a marker (or an indicator), in more specifically, an amount of the tumor marker for pancreatic cancer of the present invention [2] is preferably used as a marker (or an indicator).

In addition, when an amount of the fucosylated sugar chain in the Site 3 is used as a marker (or an indicator), the total amount of the tumor markers for pancreatic cancer of the present invention [II] and [III], or an amount of the tumor marker for pancreatic cancer of the present invention [II] or [III] is more preferable, and an amount of the tumor marker for pancreatic cancer of the present invention [III] is particularly preferable. In more specifically, the total amount of the tumor markers for pancreatic cancer of the present invention [2], [3] and [4], or an amount of any one or two types of the tumor markers for pancreatic cancer of the present invention [2], [3] and [4] is preferably used as a marker (or an indicator), and among them, an amount of tumor markers for pancreatic cancer of the present invention [3] and/or [4] is more preferable, and an amount of tumor marker for pancreatic cancer of the present invention [4] is particularly preferable.

(1) Biological Sample:

The biological sample to be used in the present invention includes tissue such as pancreatic tissue and body fluid, for example, plasma, serum, pancreatic fluid, saliva, lymphatic fluid and spinal fluid, or processed preparations thereof and the like. Among them, body fluid such as serum and plasma is useful as a test sample, and that is a characteristic point of the present invention.

(2) Measurement and Determination Procedures:

(2-1) Extraction and Purification of Haptoglobin from Biological Sample:

On the occasion of practicing the method of the present invention, usually, the objective haptoglobin is extracted from a biological sample as described above.

Such methods of extraction and purification include the methods well known per se, for example, a method using an affinity column coupled with an anti-haptoglobin antibody, an immunoprecipitation technique using anti-haptoglobin antibody, and the like.

(2-2) Decomposition of Haptoglobin into Glycopeptides (Decomposition into Each Site):

In the next place, from the haptoglobin extracted as described above, a peptide fragment (glycopeptide) containing Site 1 [asparagine at the $184^{th}$ from N-terminal (methionine terminal) of amino acid sequence of the human haptoglobin] and a peptide fragment (glycopeptide) containing Site 3 [asparagine at the $211^{th}$ from N-terminal (methionine terminal) of amino acid sequence of the human haptoglobin] are isolated.

As to separation method, the following 3 peptide fragments (glycopeptides) can be separated by the method well known per se, for example, using trypsin and lysylendopeptidase:

(a) A peptide fragment containing Site 1: a peptide fragment (glycopeptide) from methionine at the $179^{th}$ to lysine at the $202^{nd}$ from N-terminal (methionine terminal);

(b) A peptide fragment containing Site 2 and Site 3: a peptide fragment (glycopeptide) from asparagine at the $203^{th}$ to lysine at the $215^{th}$ from N-terminal (methionine terminal);

(c) A peptide fragment containing Site 4: a peptide fragment (glycopeptide) from valine at the $236^{th}$ to lysine at the $251^{st}$ from N-terminal (methionine terminal).

That is, a mixture containing the above-described 3 peptide fragments (glycopeptides) of (a)-(c) can be obtained by applying the above-described method to the extracted haptoglobin, and the resultant mixture can be used for the detection of fucosylated sugar chain in the Site 1.

Figure 2:
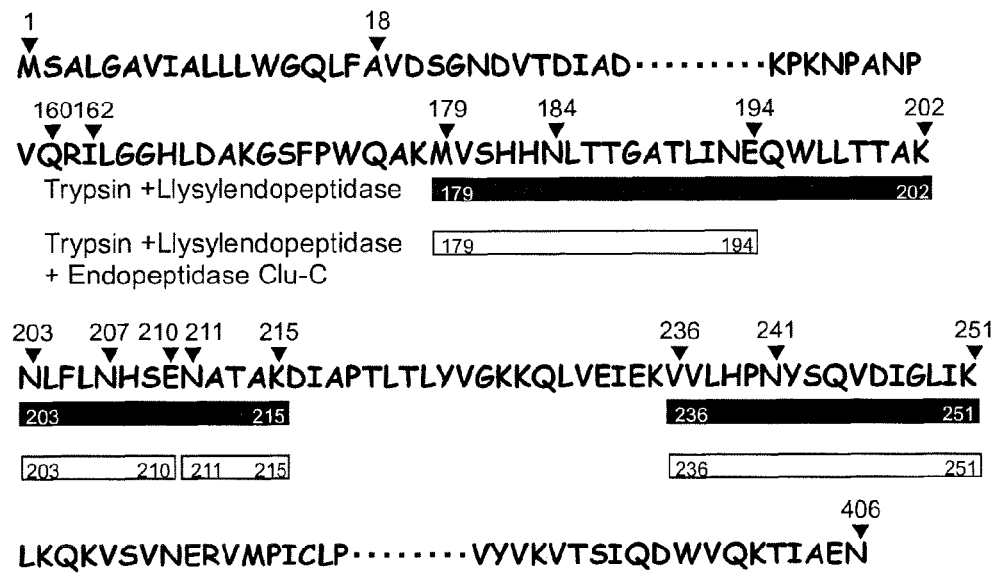
FIG. 2 shows the digestion sites (digestion fragments) in the amino acid sequence of human haptoglobin by (1) trypsin and lysylendopeptidase, and by (2) trypsin, lysylendopeptidase and endopeptidase Glu-C.

The digestion sites (digestion fragments) by trypsin and lysylendopeptidase in the amino acid sequence of the human haptoglobin are shown in FIG. 2.

In addition, the following 4 peptide fragments (glycopeptides) can be separated by the method well known per se, for example, using trypsin, lysylendopeptidase and endopeptidase Glu-C, namely, by applying endopeptidase Glu-C additionally to a mixture containing the 3 peptide fragments (glycopeptides) obtained by the above-described method:

(a') A peptide fragment containing the Site 1: a peptide fragment (glycopeptide) from methionine at the $179^{th}$ to glutamic acid at the $194^{th}$ from N-terminal (methionine terminal);

(b') A peptide fragment containing the Site 2: a peptide fragment (glycopeptide) from asparagine at the $203^{rd}$ to glutamic acid at the $210^{th}$ from N-terminal (methionine terminal);

(c') A peptide fragment containing the Site 3: a peptide fragment (glycopeptide) from asparagine at the $211^{th}$ to lysine at the $215^{th}$ from N-terminal (methionine terminal);

(d') A peptide fragment containing the Site 4: a peptide fragment (glycopeptide) from valine at the $236^{th}$ to lysine at the $251^{st}$ from N-terminal (methionine terminal).

That is, by applying the above-described method to the extracted haptoglobin, a mixture containing above-described 4 peptide fragments (glycopeptides) of (a')-(d') can be obtained, and the resultant mixture can be used for the detection of fucosylated sugar chain in the Site 1 and/or the Site 3.

The digestion sites (digestion fragments) by trypsin, lysylendopeptidase and endopeptidase Glu-C in the amino acid sequence of the human haptoglobin are shown in FIG. 2. In this FIG. 2, black frame shows the peptide fragment obtained by the treatment with trypsin and lysylendopeptidase, white frame shows the peptide fragment obtained by the treatment with trypsin, lysylendopeptidase and endopeptidase Glu-C.

If necessary, the obtained mixture containing peptide fragments (glycopeptides) may be subjected to affinity separation procedure with, for example, Sepharose CL4B to concentrate the peptide fragments (glycopeptides). Particularly, it is preferable to carry out the concentration procedure of the peptide fragment (glycopeptide), when trypsin, lysylendopeptidase and endopeptidase Glu-C are used in the above-described methods.

In addition, the obtained mixture containing peptide fragments (glycopeptides) or the extracted haptoglobin may be treated with acid (for example, acetic acid) to remove sialic acid (NeuAc) which is bound to galactose at non-reducing terminal of the sugar chain present in the aforementioned peptide fragments (desialylation). By this treatment, plural number of sialo-forms of which the structure except sialic acid (NeuAc) are the same but the number (binding mode) of sialic acid (NeuAc) bound are different can be transformed to asialo-form with the same structure by the removal of sialic acid (NeuAc). This allows to remove the sialic acid causing nonuniformity (difference in binding mode), and to make the analysis more simple and speedy in the measurement of the fucosylated sugar chain described hereinafter. Particularly, when trypsin, lysylendopeptidase and endopeptidase Glu-C are used in the method described above, number of the peptide fragment produced may increase, and in the measurement of the fucosylated sugar chain as described below, elution position of the peptide fragment coupled with fucosylated sugar chain could overlap with that of the peptide fragment not coupled with sugar chain. Therefore, in such situation, it is preferable to carry out acid treatment to prevent such overlapping.

As described above, the tumor markers for pancreatic cancer [3] and [4] of the present invention are present in the Site 3, but almost never in the other Sites. Especially, the tumor marker for pancreatic cancer [4] of the present invention is present in the test sample from the patients with pancreatic cancer, but almost never present in the test sample from the patients with chronic pancreatitis and normal volunteers. Therefore, in the method of the present invention, when the tumor markers for pancreatic cancer [3] and/or [4], particularly the tumor marker for pancreatic cancer [4] is used as an indicator, separation (isolation) of the peptide fragment (glycopeptide) comprising the Site 3 from the extracted haptoglobin is not necessary, and the extracted haptoglobin can be applied directly to the following measurement of the fucosylated sugar chain.

(2-3) Measurement of Fucosylated Sugar Chain (a Marker for Pancreatic Cancer):

By subjecting the mixture containing peptide fragments (glycopeptides) obtained as described above or the mixture containing peptide fragments (asialo-glycopeptides) obtained by acid treatment to liquid chromatography-mass spectrometry (LC-MS) well known per se, such as for example, LC-ESI MS and LC-APCI MS, detection and identification as well as measurement of an amount of the fucosylated sugar chain (peptide fragments coupled with fucosylated sugar chain) in the Site 1 and/or Site 3 can be performed.

That is, for example, through the step of liquid chromatography (HPLC) in the liquid chromatography-mass spectrometry process, the peptide fragments in the mixture are separated into the respective Sites. In the next place, through the step of mass spectrometry (MS) of the separated peptide fragments containing respective sites in the liquid chromatography-mass spectrometry process, the peptide fragment with the objective Site (Site 1 and/or 3) is identified, and further the objective fucosylated sugar chain (the peptide fragment coupled with the objective fucosylated sugar chain) in the peptide fragments with the objective Site (Site 1 and/or 3) is identified, and then the amount is measured (calculated).

More specifically, for example, when a mixture which has been treated with trypsin and lysylendopeptidase is used, the mixture is separated into 3 types of peptides by HPLC analysis: a peptide fragment with the Site 1 (the above-described (a)), a peptide fragment with the Site 2 and 3 (the above-described (b)) and a peptide fragment with the Site 4 (the above-described (c)). Then, each separated peptide with respective Site is analyzed by mass spectrometry to identify the peptide with the Site 1, and further, the objective peptide fragment coupled with fucosylated sugar chain among the identified peptides with the Site 1 is specified, then the amount of aforementioned peptide fragment is calculated. In addition, for example, when a mixture treated with trypsin, lysylendopeptidase and endopeptidase Glu-C is used, the mixture is separated into 4 types of peptides by HPLC analysis: a peptide fragment with the Site 1 (the above-described (a')), a peptide fragment with the Site 2 (the above-described (b')), a peptide fragment with the Site 3 (the above-described (c')) and a peptide fragment with the Site 4 (the above-described (d')). Then, each separated peptides with respective Sites is analyzed by mass spectrometry to identify the peptide with the Site 1 and/or the Site 3 (preferably the Site 3), and further, the objective peptide fragment coupled with fucosylated sugar chain among the identified peptides with the Site 1 and/or the Site 3 (preferably the Site 3) is specified, then the amount of the aforementioned peptide fragment is calculated.

In the foregoing description, identification of the peptide fragment with objective Site (1 and/or 3) by mass spectrometry may be carried out, for example, as follows.

Namely, for example, using the total mass number of the standard sugar chain and the above-described peptide fragments containing Site 1 and/or 3 (the above-described (a), (a'), (c')) as an indicator, and by analyzing the total mass number, the elution time (elution position) of the Site 1 and/or the elution time (elution position) of the Site 3 can be specified from the elution pattern in the mass spectrometry of the above-described mixture. That is, in the mass spectrometry, by analyzing the peak corresponding to the total mass number of the standard sugar chain and the peptide fragment containing Site 1 (the above-described (a), (a')), the peak appearing near the elution time (elution position) at which a peak with a high intensity appears can be specified as a peak assigned to the peptide fragment (glycopeptide) with the Site 1. In addition, in the mass spectrometry, by analyzing the peak corresponding to the total mass number of the standard sugar chain and the peptide fragment containing Site 3 (the above-described (c')), the peak appearing near the elution time (elution position) at which a peak with a high intensity appears can be specified as a peak assigned to the peptide fragment (glycopeptide) with the Site 3.

It should be noted that the standard sugar chain used here is, for example, the sugar chain which is known to be present in large amount in the haptpblobin, specifically, the sugar chain shown by the above-described structural formula [I] or the sialo-form (particularly disialo-form) thereof, and the like.

In addition, in the foregoing description, the total mass number to be used as an indicator includes, for example, the combination of the standard sugar chain and the peptide fragment as shown below.

(1) In the case where the haptoglobin is digested with trypsin and lysylendopeptidase;

An indicator for specifying Site 1 (in the case with no acid treatment): a peptide fragment from methionine at the $179^{th}$ to lysine at the $202^{nd}$ from N-terminal (methionine terminal) and the sugar chain shown by the above-described structural formula [I];

An indicator for specifying Site 1 (in the case with acid treatment): a peptide fragment from methionine at the $179^{th}$ to lysine at the $202^{nd}$ from N-terminal (methionine terminal) and the sialo-form (particularly, disialo-form) of the sugar chain shown by the above-described structural formula [I];

(2) In the case where the haptoglobin is digested with trypsin, lysylendopeptidase and endopeptidase Glu-C;

An indicator for specifying Site 1 (in the case with no acid treatment): a peptide fragment from methionine at the $179^{th}$ to glutamic acid at the $194^{th}$ from N-terminal (methionine terminal) and the sugar chain shown by the above-described structural formula [I];

An indicator for specifying Site 1 (in the case with acid treatment): a peptide fragment from methionine at the $179^{th}$ to glutamic acid at the $194^{th}$ from N-terminal (methionine terminal) and the sialo-form (particularly, disialo-form) of the sugar chain shown by the above-described structural formula [I];

An indicator for specifying Site 3 (in the case with no acid treatment): a peptide fragment from asparagine at the $211^{th}$ to lysine at the $215^{th}$ from N-terminal (methionine terminal) and the sugar chain shown by the above-described structural formula [I];

An indicator for specifying Site 3 (in the case of acid treatment): a peptide fragment from asparagine at the $211^{th}$ to lysine at the $215^{th}$ from N-terminal (methionine terminal) and the sialo-form (particularly, disialo-form) of the sugar chain shown by the above-described structural formula [I].

In addition, identification of the objective fucosylated sugar chain (peptide fragment coupled with the objective fucosylated sugar chain) from each peptide fragment analyzed by mass spectrometry and measurement (calculation) of its amount may be carried out as follows.

That is, as shown in Examples described below, for example, from the mass number of each peak of the objective Sites obtained by mass spectrometry, the carbohydrate structure corresponding to each peak (mass number) is determined based on the structure of the standard sugar chain used as an indicator for identifying the objective Site. In other words, the mass number assigned to the sugar chain is calculated by subtracting the mass number of the peptide fragment with the objective Site from the mass number of each peak, and the corresponding carbohydrate structure is determined from the calculated mass number assigned to the sugar chain. Subsequently, among the determined carbohydrate structures, the peptide fragment coupled with the objective fucosylated sugar chain is specified, and an amount of the aforementioned peptide fragment (glycopeptide) is calculated from the peak intensity of the peptide fragment coupled with the specified objective fucosylated sugar chain.

In addition, for example, in the same manner as described above, the structure and the mass number of the peptide fragment (glycopeptide) having sugar chain are determined and calculated for each objective Site in advance, and by comparing this mass number with the actually measured mass numbers of the peaks corresponding to the respective peptide fragments having each sugar chain, the peptide fragment coupled with the objective fucosylated sugar chain is specified, and in the same time, from the (ion) intensity of the peak of the specified aforementioned peptide fragment (glycopeptide), an amount of the aforementioned peptide fragment (glycopeptide) may be calculated directly.

Specifically, calculation of the amount of peptide fragment coupled with the objective fucosylated sugar chain may be carried out as described below.

(a) Amount of Fucosylated Sugar Chain in the Site 1:

From the mass spectrum of the specified Site 1, all peaks corresponding to the peptide fragments (glycopeptides) coupled with fucosylated sugar chain (namely, all peaks corresponding to asialo-glycopeptides having fucosylated sugar chain, or in addition to this, the peaks corresponding to each of plural number of sialo-glycopeptides having fucosylated sugar chain) are specified, and then the ion intensities of these peaks are calculated, and the amount is obtained by combining them.

(b) Amount of Fucosylated Sugar Chain in Site 3:

From the mass spectrum of the specified Site 3, all peaks corresponding to the peptide fragments (glycopeptides) coupled with fucosylated sugar chain (namely, all peaks corresponding to asialo-glycopeptides having fucosylated sugar chain, or in addition to this, the peaks corresponding to each of plural number of sialo-glycopeptides having fucosylated sugar chain) are specified, and then the ion intensities of these peaks are calculated, and the amount is obtained by combining them.

(c) Total Amount of Fucosylated Sugar Chain in Both Site 1 and Site 3:

The above-described (a) and (b) are totalized.

(d) Tumor Marker for Pancreatic Cancer [I] of the Present Invention:

From the mass spectra of the specified objective Site (1 and/or 3), all peaks corresponding to the peptide fragments (the peptide fragments having the tumor marker for pancreatic cancer [I] of the present invention: glycopeptides) coupled with the fucosylated sugar chain having a structure of the structural formula [I] (namely, the peaks corresponding to the fucosylated asialo-glycopeptides having a structure of the structural formula [I], or in addition to this, the peaks corresponding to each of plural number of fucosylated sialo-glycopeptides having a structure of the structural formula [I]) are specified, and then the ion intensities of these peaks are calculated, and the amount is obtained by combining them.

(e) Tumor Marker for Pancreatic Cancer [II] of the Present Invention:

From the mass spectra of the specified objective Site (1 and/or 3), all peaks corresponding to the peptide fragments (the peptide fragments having the tumor marker for pancreatic cancer [II] of the present invention: glycopeptides) coupled with fucosylated sugar chain having a structure of the structural formula [III] (namely, the peaks corresponding to fucosylated asialo-glycopeptides having a structure of the structural formula [II], or in addition to this, the peaks corresponding to each of plural number of fucosylated sialo-glycopeptides having a structure of the structural formula [II]) are specified, and then the ion intensities of these peaks are calculated, and the amount is obtained by combining them.

(f) Tumor Marker for Pancreatic Cancer [III] of the Present Invention:

From the mass spectra of the specified objective Site (1 and/or 3), all peaks corresponding to the peptide fragments (the peptide fragments having the tumor marker for pancreatic cancer [III] of the present invention: glycopeptides) coupled with fucosylated sugar chain having a structure of the structural formula [III] (namely, the peaks corresponding to fucosylated asialo-glycopeptides having a structure of the structural formula [III], or in addition to this, the peaks corresponding to each of plural number of fucosylated sialo-glycopeptides having a structure of the structural formula [III]) are specified, and then the ion intensities of these peaks are calculated, and the amount is obtained by combining them.

(g) Total Amount of the Tumor Markers for Pancreatic Cancer [I], [II] and [III] of the Present Invention:

The above-described (d), (e) and (f) are totalized.

(h) Amount of 2 Types Among the Tumor Markers for Pancreatic Cancer [I], [II] and [III] of the Present Invention:

From the above-described (d)-(f), the objective 2 types are totalized.

(i) Amount of the Tumor Marker for Pancreatic Cancer [1] of the Present Invention:

From the mass spectra of the specified objective Site (1 and/or 3), all peaks corresponding to the peptide fragments (the peptide fragments having the tumor marker for pancreatic cancer [1] of the present invention: glycopeptides) coupled with sugar chain having a structure of the structural formula [1] (namely, the peaks corresponding to asialo-glycopeptides having a structure of the structural formula [1], or in addition to this, the peaks corresponding to each of plural number of sialo-glycopeptides having a structure of the structural formula [1]) are specified, and then the ion intensities of these peaks are calculated, and the amount is obtained by combining them.

(j) Amount of the Tumor Marker for Pancreatic Cancer [2] of the Present Invention:

From the mass spectra of the specified objective Site (1 and/or 3), all peaks corresponding to the peptide fragments (the peptide fragments having the tumor marker for pancreatic cancer [2] of the present invention: glycopeptides) coupled with sugar chain having a structure of the structural formula [2] (namely, the peaks corresponding to asialo-glycopeptides having a structure of the structural formula [2], or in addition to this, the peaks corresponding to each of plural number of sialo-glycopeptides having a structure of the structural formula [2]) are specified, and then the ion intensities of these peaks are calculated, and the amount is obtained by combining them.

(k) Amount of the Tumor Marker for Pancreatic Cancer [3] of the Present Invention:

From the mass spectra of the specified objective Site (1 and/or 3), all peaks corresponding to the peptide fragments (the peptide fragments having the tumor marker for pancreatic cancer [3] of the present invention: glycopeptides) coupled with sugar chain having a structure of the structural formula [3] (namely, the peaks corresponding to asialo-glycopeptides having a structure of the structural formula [3], or in addition to this, the peaks corresponding to each of plural number of sialo-glycopeptides having a structure of the structural formula [3]) are specified, and then the ion intensities of these peaks are calculated, and the amount is obtained by combining them.

(l) Amount of the Tumor Marker for Pancreatic Cancer [4] of the Present Invention:

From the mass spectra of the specified objective Site (1 and/or 3), all peaks corresponding to the peptide fragments (the peptide fragments having the tumor marker for pancreatic cancer [4] of the present invention: glycopeptides) coupled with sugar chain having a structure of the structural formula [4] (namely, the peaks corresponding to asialo-glycopeptides having a structure of the structural formula [4], or in addition to this, the peaks corresponding to each of plural number of sialo-glycopeptides having a structure of the structural formula [4]) are specified, and then the ion intensities of these peaks are calculated, and the amount is obtained by combining them.

(m) Total Amount of the Tumor Marker for Pancreatic Cancer [1], [2], [3] and [4] of the Present Invention:

The amounts of the above-described (i), (j), (k) and (l) are totalized.

(n) Amount of Any 2 Types or 3 Types of the Tumor Markers for Pancreatic Cancer [1], [2], [3] and [4] of the Present Invention:

From the above-described items (i)-(l), the amount of the objective 2 types or 3 types are totalized.

In the method described above, when a mixture containing non-acid-treated peptide fragments (glycopeptide) is used, there is a possibility of existence of plural number of peptide fragments (sialo-glycopeptides) in the mixture with the same structure except for sialic acid (NeuAc), but having sugar chain with different number of sialic acid (NeuAc) (sialoform) Since these plural number of peptide fragments (sialo-glycopeptides) are different in the number of sialic acid (NeuAc) attached, these will be separated and measured for each fragment with different mass in the mass spectrometry. Therefore, in such case, as shown in the items (a)-(n) above, from each separated and measured peak with different mass, all peaks corresponding to the sialo-glycopeptides having objective fucosylated sugar chain and the peaks corresponding to the asialo-glycopeptides having objective fucosylated sugar chain are specified, and then the ion intensities of these peaks may be totalized.

In the method of determining pancreatic cancer of the present invention, the amount of the objective fucosylated sugar chain (the peptide fragment coupled with objective fucosylated sugar chain) itself (above described (a)-(n)) may be used as a marker (or an indicator) for the determination (diagnosis, test) of pancreatic cancer, and also, for example, based on the total amount of the sugar chain (the peptide fragment coupled with sugar chain) in the objective Site (1 and/or 3) as 100%, the relative value [the relative abundance (%)] of the amount of the objective fucosylated sugar chain (the peptide fragment coupled with objective fucosylated sugar chain) in the same Site is calculated, and this may also be used as a marker (or an indicator) for the determination (diagnosis, test) of pancreatic cancer.

Here, the relative abundance (%) can be calculated as the peak (signal) intensity of the objective fucosylated sugar chain (the peptide fragment coupled with objective fucosylated sugar chain) based on the peak (signal) intensities corresponding to all sugar chains (all peptide fragments coupled with sugar chain) detected and determined in the above-described mass spectrometry as 100%, and actual calculation can be carried out as follows.

(a') Relative Abundance (%) of Fucosylated Sugar Chain in the Site 1:

From the mass spectrum of the specified Site 1, regardless of whether fucosylated or not, all peaks corresponding to the peptide fragments (glycopeptides) coupled with sugar chain (namely, all peaks corresponding to asialo-glycopeptides having sugar chain, or in addition to this, the peaks corresponding to each of plural number of sialo-glycopeptides having sugar chain) are specified, and then the ion intensities of them are calculated and totalized. Then, based on the total value as 100%, the relative value of the amount of fucosylated sugar chain in the Site 1 calculated in the above (a) is calculated.

(b') Relative Abundance (%) of Fucosylated Sugar Chain in the Site 3:

From the mass spectrum of the specified Site 3, regardless of whether fucosylated or not, all peaks corresponding to the peptide fragments (glycopeptides) coupled with sugar chain (namely, all peaks corresponding to asialo-glycopeptides having sugar chain, or in addition to this, the peaks corresponding to each of plural number of sialo-glycopeptides having sugar chain) are specified, and then the ion intensities of them are calculated and totalized. Then, based on the total value as 100%, the relative value of the amount of fucosylated sugar chain in the Site 3 calculated in the above (b) is calculated.

(c') Relative Abundance (%) of Fucosylated Sugar Chains in Both the Site 1 and Site 3:

From the mass spectra of the specified Site 1 and Site 3, regardless of whether fucosylated or not, all peaks corresponding to the peptide fragments (glycopeptides) coupled with sugar chain (namely, all peaks corresponding to asialo-glycopeptides having sugar chain, or in addition to this, the peaks corresponding to each of plural number of sialo-glycopeptides having sugar chain) are specified, and then the ion intensities of them are calculated and totalized. Then, based on the total value as 100%, the relative value of the amount of fucosylated sugar chain in both the Site 1 and Site 3 calculated in the above (c) is calculated.

(d') Relative Abundance (%) of the Tumor Marker for Pancreatic Cancer [I] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the amount of the tumor marker for pancreatic cancer [I] of the present invention in the objective Site (1 and/or 3) calculated in the above (d) is calculated.

(e') Relative Abundance (%) of the Tumor Marker for Pancreatic Cancer [II] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the amount of the tumor marker for pancreatic cancer [II] of the present invention in the objective Site (1 and/or 3) calculated in the above (e) is calculated.

(f') Relative Abundance (%) of the Tumor Marker for Pancreatic Cancer [III] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the amount of the tumor marker for pancreatic cancer [III] of the present invention in the objective Site (1 and/or 3) calculated in the above (f) is calculated.

(g') Relative Abundance (%) of the Tumor Markers for Pancreatic Cancer [I], [II] and [III] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the total amount of the tumor markers for pancreatic cancer [I], [II] and [III] of the present invention in the objective Site (1 and/or 3) calculated in the above (g) is calculated.

(h') Relative Abundance (%) of 2 Types Selected From the Tumor Markers for Pancreatic Cancer [I], [II] and [III] of the Present Invention:

From the mass spectra of the specified objective Site (1 and/or 3), regardless of whether fucosylated or not, all peaks corresponding to the peptide fragments (glycopeptides) coupled with sugar chain (namely, all the peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the total amount of 2 types selected from the tumor marker for pancreatic cancer [I], [II] and [III] of the present invention in the objective Site (1 and/or 3) calculated in the above (h) is calculated.

(i') Relative Abundance (%) of the Tumor Marker for Pancreatic Cancer [1] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the amount of the tumor marker for pancreatic cancer

[1] of the present invention in the objective Site (1 and/or 3) calculated in the above (i) is calculated.

(j') Relative Abundance (%) of the Tumor Marker for Pancreatic Cancer [2] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the amount of the tumor marker for pancreatic cancer [2] of the present invention in the objective Site (1 and/or 3) calculated in the above (j) is calculated.

(k') Relative Abundance (%) of the Tumor Marker for Pancreatic Cancer [3] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the amount of the tumor marker for pancreatic cancer [3] of the present invention in the objective Site (1 and/or 3) calculated in the above (k) is calculated.

(l') Relative Abundance (%) of the Tumor Marker for Pancreatic Cancer [4] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the amount of the tumor marker for pancreatic cancer [4] of the present invention in the objective Site (1 and/or 3) calculated in the above (1) is calculated.

(m') Relative Abundance (%) of the Tumor Markers for Pancreatic Cancer [1], [2], [3] and [4] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensity of these peaks are calculated and totalized. Then, based on the total value as 100%, the relative value of the total amount of the tumor marker for pancreatic cancer [1], [2], [3] and [4] of the present invention in the objective Site (1 and/or 3) calculated in the above (m) is calculated.

(n') Relative Abundance (%) of Any 2 Types or 3 Types Among the Tumor Markers for Pancreatic Cancer [1], [2], [3] and [4] of the Present Invention:

From the mass spectra of the specified objective Site (1 and/or 3), regardless of whether fucosylated or not, all peaks corresponding to the peptide fragments (glycopeptides) coupled with sugar chain (namely, all peaks corresponding to the asialo-glycopeptides having sugar chain, or in addition to this, the peaks corresponding to each of plural number of sialo-glycopeptides having sugar chain) are specified, and then the ion intensities of these peaks are calculated and totalized. Then, based on the total value as 100%, the relative value of the total amount of any 2 types or 3 types among the tumor markers for pancreatic cancer [1], [2], [3] and [4] of the present invention in the objective Site (1 and/or 3) calculated in the above (n) is calculated.

(2-4) Method of Determining Pancreatic Cancer:

The information (for example, the amount itself, the relative abundance, and the like) obtained by the above-mentioned methods about the amount of the peptide fragment coupled with objective fucosylated sugar chain (the fucosylated sugar chain: the tumor marker for pancreatic cancer of the present invention) is useful for determining (diagnosing, testing) pancreatic cancer.

That is, for example, the amount or the relative abundance (%) of the peptide fragment (the fucosylated sugar chain: the tumor marker for pancreatic cancer of the present invention) coupled with the objective fucosylated sugar chain in a biological sample obtained from a test subject is compared with an amount or a relative abundance (%) of the peptide fragment (the fucosylated sugar chain: the tumor marker for pancreatic cancer of the present invention) coupled with the objective fucosylated sugar chain in a biological sample obtained from a normal volunteer, and the difference or the ratio between them is obtained. From a test result that the amount or the relative abundance (%) of the peptide fragment (the fucosylated sugar chain: the tumor marker for pancreatic cancer of the present invention) coupled with the objective fucosylated sugar chain in the test subject is greater compared with that in the normal volunteer (a significant difference is observed), it can be determined that the test subject might have or may be at high risk of pancreatic cancer. Alternatively, from a test result that, between the test subject and the normal volunteer, no significant difference in the amount or the relative abundance (%) of the peptide fragment (the fucosylated sugar chain: the tumor marker for pancreatic cancer of the present invention) coupled with the objective fucosylated sugar chain is observed, it can be determined that the test subject may not have or may be no risk of pancreatic cancer.

In addition, by establishing a criterion measure (threshold value, cutoff value) in advance, from the test result that the amount or the relative abundance (%) of the peptide fragment (the fucosylated sugar chain: the tumor marker for pancreatic cancer of the present invention) coupled with the objective fucosylated sugar chain is greater than the criterion measure (threshold value, cutoff value), it can be determined that the test subject might have or may be at high risk of pancreatic cancer can be provided. Also, by establishing plural number of criterion ranges (classifications, levels) [for example, (1) no risk of pancreatic cancer, (2) low risk of pancreatic cancer, (3) a sign of pancreatic cancer and (4) high risk of pancreatic cancer, etc.], corresponding to quantitative ranges or relative value ranges of amount or relative abundance (%) of the peptide fragment (the fucosylated sugar chain: the tumor marker for pancreatic cancer of the present invention) coupled with the objective fucosylated sugar chain, it can be determined which criterion range the test result falls in.

Further more, in the same test subject, the amount or the relative abundance (%) of the peptide fragment (the fucosylated sugar chain: the tumor marker for pancreatic cancer of the present invention) coupled with the objective fucosylated sugar chain in a biological sample measured at a certain point of time is compared with the amount or the relative abundance (%) of the peptide fragment (the fucosylated sugar chain: the tumor marker for pancreatic cancer of the present invention) coupled with the objective fucosylated sugar chain measured at different point of time, and by the assessment of existence or non-existence of increase or decrease and/or of degree of increase or decrease in the amount or the relative abundance (%) of the peptide fragment (the fucosylated sugar chain: the tumor marker for pancreatic cancer of the present invention) coupled with the objective fucosylated sugar chain, diagnosis of progression stage or malignancy of pancreatic cancer, or postoperative prognosis of pancreatic cancer can be performed. Namely, from a test result that the amount or the relative abundance (%) of the peptide fragment (the fucosylated sugar chain: the tumor marker for pancreatic cancer of the present invention) coupled with the objective fucosylated sugar chain is found to be increased, it can be judged that pathological state has progressed toward pancreatic cancer (or malignancy of pancreatic cancer has increased), or a sign of progression of the pathological state toward pancreatic cancer is observed (or a sign of increased malignancy of pancreatic cancer is observed); and from a test result that the amount or the relative abundance (%) of the peptide fragment (the fucosylated sugar chain: the tumor marker for pancreatic cancer of the present invention) coupled with the objective fucosylated sugar chain in the biological sample from the test subject is found to be decreased, it can be judged that pathological state of pancreatic cancer has been improved, or a sign of improvement of the pathological state of pancreatic cancer is observed. In addition, from a test result that the amount or the relative abundance (%) of the peptide fragment (the fucosylated sugar chain: the tumor marker for pancreatic cancer of the present invention) coupled with the objective fucosylated sugar chain is found to be not changed, it can be judged that pathological state of pancreatic cancer has not been changed.

Hereinafter, the present invention will be further illustrated more specifically based on the following Examples and Comparative Examples, however, the scope of the present invention should not be limited thereto.

Example 1

Test Sample

Experiments were carried out using serum samples from 5 patients with pancreatic cancer (PC) (PC1-5: 2 males, 3 females, 65 years old of average age), 5 patients with chronic pancreatitis (CP) (CP1-5: 3 males, 2 females, 66 years old of average age), and 8 normal volunteers (NV) (NV1-8: 5 males, 3 females, 46 years old of average age). Among 8 normal volunteers, 5 persons were 26-38 years old [NV(<40): NV1-5] and 3 persons were 63-75 years old [NV(>60): NV6-8]. The serum samples were kept frozen at −80° C. immediately after the blood has been drawn until measurement.

Extraction and Purification of Haptoglobin

After 100 µl each of serum from a patient with pancreatic cancer and a patient with chronic pancreatitis, and 300 µl of serum from a normal volunteer were filtrated through a 0.45 µm filter (Minisart RC 15, Sartorius, Goettingen, Germany), each serum sample was diluted with buffer A (50 mM Sodium phosphate buffer, 0.5 M NaCl, 0.02% $NaN_3$, pH 7.4) to make a volume of 7 ml. The diluted serum sample was applied to an anti-haptoglobin antibody affinity column. The anti-haptoglobin antibody affinity column was prepared according to the conventional procedure by binding 300 µl of anti-haptoglobin antibody (DakoCytomation, Glostrup, Denmark) to 1 ml of HiTrap NHS-activated HP (GE Healthcare, Uppsala, Sweden). After the diluted serum sample was circulated 5 times through the column at room temperature using a peristaltic pump, the column was washed with 15 ml of the buffer A. After washing the column, haptoglobin was eluted with 5 ml of elute (100 mM Glycine, 0.5 M NaCl, pH 3.0). The value of pH of the eluted haptoglobin solution was adjusted to around neutral using 100 µl of 2 M Tris-HCl (pH 8), and after that the buffer solution was replaced by purified water using a PD-10 column (GE Healthcare, Uppsala, Sweden). The solution was evaporated to dryness under reduced pressure, and then the residue was dissolved in 100 µl of purified water (Sample solution A).

Analysis of Carbohydrate Structure of the Site 1 and the Site 4 Using LC-ESI MS (1) Digestion of Haptoglobin by Trypsin and Lysylendopeptidase:

After 80 µl of Sample solution A was evaporated to dryness under reduced pressure, 500 µl of buffer solution B (250 mM Tris-HCl, 6 M guanidine hydrochloride, 2 mM EDTA, 10 mg dithiothreitol, pH 8.5) was added thereto and reconstituted. This solution was incubated at 50° C. for 1 hour, and then 20 mg of iodoacetamide was added thereto, and further incubated in the dark at room temperature for 30 minutes. In the next place, the solvent of this solution was replaced by 0.05 N hydrochloric acid solution using a Nap-5 column (GE Healthcare, Uppsala, Sweden). After adjusting pH of 1 ml of the replaced solution to nearly neutral using 100 µl of 1 M Tris-HCl (pH 9.0), an enzyme solution prepared by dissolving 2 µg of lysylendopeptidase and 2 µg of trypsin in 20 µl of 50 mM Tris-HCl (pH 8.5) was added and incubated at 37° C. for 16 hours. The solution was boiled, and then evaporated to dryness under reduced pressure. The residue was dissolved in 100 µg of purified water (Sample solution B).

(2) LC-ESI MS Analysis:

Ten (10) µl of the resultant Sample solution B was subjected to separation analysis using an ODS column (Develosil 300ODS-HG-5, 150×1.0 mm i.d., Nomura Chemical Co., Ltd., Japan) under the following conditions. As a mobile phase, (A) 0.1% TFA (trifluoroacetic acid) and (B) 0.1% TFA/80% acetonitrile were used. For the analysis, Agilent 1100 series HPLC system was used, and elution was carried out at a flow rate of 50 µl/min, with gradient concentration of the solution (B) from 10% to 60% over 80 minutes. The eluate was introduced continuously into an electrospray ionization mass spectrometer (Esquire HCT, Bruker Daltonics GmbsH, Bremen, Germany).

Results of the analysis are described below.

a) Confirmation of Elution Position of Peptides Present in the Sample:

In order to confirm the positions where the peptides and the glycopeptides are present in the sample obtained above, analysis of BPC (Base Peak Chromatography) was carried out.

It should be noted that BPC refers to chromatogram indicating only an ion intensity of the ion peak with highest intensity at each time point in the MS/MSMS scanning.

Results are shown as BPC in FIG. 3A. It should be noted that the BPC in FIG. 3A indicates the peaks with greatest intensities in both MS scan and MSMS scan repeated at intervals of 1.5 seconds.

b) Preliminary Identification of Elution Positions of the Glycopeptide Containing Site 1 and the Glycopeptide Containing Site 4:

In order to identify preliminarily elution positions of the glycopeptides containing Site 1 and Site 4, analysis of the following EIC (Extracted Ion Chromatogram) was carried out.

In the case of a complex-type oligosaccharide of Asn-type (carbohydrate compound having a very complicated structure), since the NeuAc-Gal-GlcNAc (mass number: $[M+H]^+=657.3$ m/z) is susceptible to fragmentation in MSMS measurement, elution positions of the peptides having sugar chain can be identified by analyzing their mass numbers.

The EIC of MSMS (at m/z 657.3) in FIG. 3A is a chromatogram indicating peak intensities of the fragment ion having a mass number of 657.3 m/z generated in the MSMS measurement of a test sample from normal volunteer (NV5).

As a result, peaks with high peak intensities were found at 40, 61 and 68 minutes in the chromatogram.

c) Identification of an Elution Position of the Glycopeptides Containing Site 1:

In order to identify peak positions of the glycopeptides containing Site 1, intensities of the ion peak having a mass number ($[M+4H]^{4+}=1221.8$ m/z) of glycopeptide coupled with a sialic acid-bound biantennary N-glycan (disialo-biantennary N-glycan) sugar chain (the sugar chain shown by 2-N2 in FIG. 4 as described later) known as the principal carbohydrate structure of haptoglobin was analyzed.

The EIC of MS (at 1221.8-1222.8 m/z) Site 1 in FIG. 3A is a chromatogram showing peak intensities of the fragment ions having mass numbers of 1221.8-1222.8 m/z generated in the MS measurement of a test sample from normal volunteer (NV5).

As a result, an elution position of the peak showing high intensity was found at around 68 minutes in the chromatogram. This was in good agreement with the elution position of 68 minutes obtained in the above b) for the NeuAc-Gal-GlcNAc (mass number: $[M+H]^+=657.3$ m/z) derived from a complex type oligosaccharide of Asn-type in MSMS measurement.

From the results described above, the peak at around 68 minutes was identified as the peak assigned to the glycopeptide containing Site 1.

Though not shown in the figure, for both cases, where the test sample from a patient with pancreatic cancer (PC) was used and where the test sample from a patient with chronic pancreatitis (CP) was used, analyses were carried out in the same manner as described above, and peaks at around 68 minutes were identified as the peaks assigned to the glycopeptides containing Site 1.

d) Identification of Elution Position of the Glycopeptides Containing Site 4:

In the same manner as described in the above c), in order to identify the peak position of the glycopeptides containing Site 4, intensity of the ion peak having a mass number ($[M+3H]^{3+}=1333.9$ m/z) of glycopeptide coupled with a sialic acid bound biantennary N-glycan (disialo-biantennary N-glycan) sugar chain (the sugar chain shown by 2-N2 in FIG. 4 as described later) known as the principal carbohydrate structure of haptoglobin was analyzed.

The EIC of MS (at 1333.9-1334.9 m/z) Site 4 in FIG. 3A is a chromatogram indicating peak intensity of the fragment ions having mass numbers of 1333.9-1334.9 m/z generated in the MS measurement of a test sample from normal volunteer (NV5).

As a result, an elution position of the peak showing high intensity was found at around 61 minutes in the chromatogram. This was in good agreement with the elution position of 61 minutes obtained in the above-described b) for the NeuAc-Gal-GlcNAc (mass number: $[M+H]^+=657.3$ m/z) derived from a complex type oligosaccharide of Asn-type in MSMS measurement.

From the results stated above, the peak at around 61 minutes was identified as the peak assigned to the glycopeptide containing Site 4.

Though not shown in the figure, for both cases, where the test sample from a patient with pancreatic cancer (PC) was used and where the test sample from a patient with chronic pancreatitis (CP) was used, analyses were carried out in the same manner as described above, and the peaks at around 61 minutes were identified as the peaks assigned to the glycopeptides containing Site 4.

In the same manner, results of identification of the peak positions of the glycopeptide containing both Site 2 and Site 3 are shown as EIC of MS (at 1467.8-1468.8 m/z) Site 2-3 in FIG. 3A.

The EIC of MS (at 1467.8-1468.8 m/z) Site 2-3 in FIG. 3A is a chromatogram indicating peak intensities of the fragment ion having mass numbers of 1467.8-1468.8 m/z generated in the MS measurement of a test sample from normal volunteer (NV5).

e) Determination of Carbohydrate Structure in the Site 1 of Haptoglobin:

Averaging of mass spectra near the elution positions (67-72 minutes) specified in the above-described c) for the glycopeptides containing Site 1 was carried out for each test sample from a normal volunteer (NV5), a patient with chronic pancreatitis (CP4) and a patient with pancreatic cancer (PC5).

Results are shown in FIG. 3B.

In addition, as shown in FIG. 4, the glycopeptides which contain Site 1 having various presumable types of carbohydrate structures and the mass numbers thereof were calculated.

From the relationship between the calculated mass numbers as shown in FIG. 4 and the presumed various types of carbohydrate structures, and also from the mass numbers of the peaks obtained for each test sample as shown in FIG. 3B, carbohydrate structure of each peak was determined.

Figure 3:
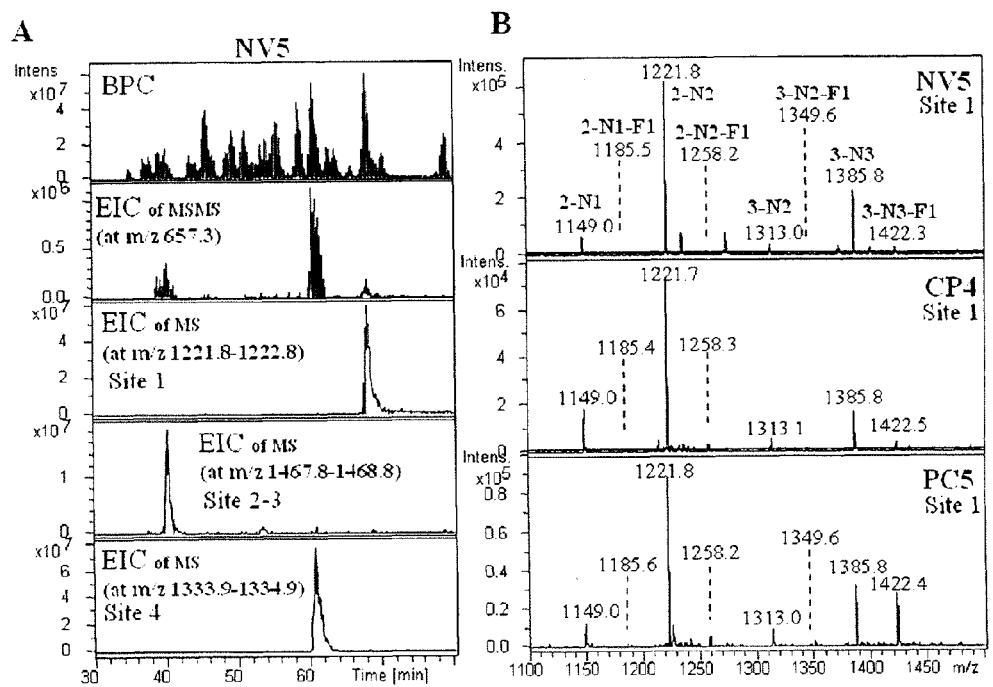
FIG. 3 shows the followings.

It should be noted that the first numeral put on the abbreviations of carbohydrate structures in FIG. 3 and FIG. 4 indicates number of branch; N and following numeral indicate number of NeuAc; and also F and following numeral indicate number of fucosylation.

In Table 1, carbohydrate structures in the Site 1 determined for each test sample from a normal volunteer (NV5), a patient with chronic pancreatitis (CP4) and a patient with pancreatic cancer (PC5) are shown.

TABLE 1

| Carbohydrate structure | Sample from normal volunteer | Sample from patient with chronic pancreatitis | Sample from patient with pancreatic cancer |
| --- | --- | --- | --- |
| 2-N1 | ○ | ○ | ○ |
| 2-N1-F1 | ○ | ○ | ○ |
| 2-N2 | ○ | ○ | ○ |
| 2-N2-F1 | ○ | ○ | ○ |
| 3-N2 | ○ | ○ | ○ |
| 3-N2-F1 | ○ | X | ○ |
| 3-N3 | ○ | ○ | ○ |
| 3-N3-F1 | ○ | ○ | ○ |
| 4-N1 | X | X | X |
| 4-N1-F1 | X | X | X |

TABLE 1-continued

| Carbohydrate structure | Sample from normal volunteer | Sample from patient with chronic pancreatitis | Sample from patient with pancreatic cancer |
|---|---|---|---|
| 4-N2 | X | X | X |
| 4-N2-F1 | X | X | X |
| 4-N3 | X | X | X |
| 4-N3-F1 | X | X | X |
| 4-N4 | X | X | X |
| 4-N4-F1 | X | X | X | f) Determination of Carbohydrate Structure in the Site 4 of Haptoglobin:

Averaging of mass spectra near the elution positions (59-64 minutes) specified in the above-described d) for the glycopeptides containing Site 4 was carried out for each test sample from a normal volunteer (NV5), a patient with chronic pancreatitis (CP4) and a patient with pancreatic cancer (PC5) (It should be noted that the results of the mass spectrum were not specifically shown.), and then the carbohydrate structure of each peak was determined in the same manner as in the above e).

In Table 2, carbohydrate structures in the Site 4 determined for each test sample from a normal volunteer (NV5), a patient with chronic pancreatitis (CP4) and a patient with pancreatic cancer (PC5) are shown.

TABLE 2

| Carbohydrate structure | Sample from normal volunteer | Sample from patient with chronic pancreatitis | Sample from patient with pancreatic cancer |
|---|---|---|---|
| 2-N1 | ◯ | ◯ | ◯ |
| 2-N1-F1 | X | ◯ | ◯ |
| 2-N2 | ◯ | ◯ | ◯ |
| 2-N2-F1 | ◯ | ◯ | ◯ |
| 3-N2 | ◯ | ◯ | ◯ |
| 3-N2-F1 | ◯ | ◯ | ◯ |
| 3-N3 | ◯ | ◯ | ◯ |
| 3-N3-F1 | ◯ | ◯ | ◯ |
| 4-N1 | ◯ | ◯ | ◯ |
| 4-N1-F1 | X | ◯ | X |
| 4-N2 | ◯ | ◯ | ◯ |
| 4-N2-F1 | ◯ | ◯ | ◯ |
| 4-N3 | ◯ | ◯ | ◯ |
| 4-N3-F1 | X | ◯ | ◯ |
| 4-N4 | ◯ | ◯ | ◯ |
| 4-N4-F1 | ◯ | ◯ | ◯ |

Analysis of Carbohydrate Structure in the Site 2 and the Site 3 Using LC-ESI MS (1) Digestion of Haptoglobin by Trypsin, Lysylendopeptidase and Endopeptidase Glu-C:

After 150 µl of purified water was added to 50 µl of Sample solution B (which has been treated with trypsin and lysylendopeptidase), 1 ml of 1-buthanol/ethanol solution (4:1, v/v) was further added thereto and mixed well. This solution was transferred to a polypropylene tube of 1.5 ml volume containing 100 µl of Sepharose CL4B which was equilibrated with 1-buthanol/ethanol/purified water solution (4:1:1, v/v) in advance. After shaking the mixture gently for 30 minutes, the gel was washed 3 times with 1 ml of 1-buthanol/ethanol/purified water solution (4:1:1, v/v). Further, the gel was incubated in ethanol/purified water (1:1, v/v) for 10 minutes, after that, the liquid phase was separated and evaporated to dryness under reduced pressure.

(2) Desialylation of Glycopeptide by Acid Treatment:

To the residue produced by evaporation to dryness under reduced pressure obtained in the above-described (1), 100 µl of 2 M acetic acid was added and incubated at 80° C. for 2 hours to remove sialic acid, then the solution was evaporated to dryness under reduced pressure. After the residue was dissolved in 40 µl of purified water, to 10 µl of this solution, 30 µl of endoproteinase Glu-C solution (30 µl of 50 mM $NH_4HCO_3$ solution containing 1 µg of Glu-C) was added, and incubated at 37° C. for 16 hours, then boiled (Sample solution C).

(3) LC-ESI MS Analysis:

Ten (10) µl of the resultant Sample solution C was subjected to separation analysis using an ODS column (Develosil 300ODS-HG-5, 150×1.0 mm i.d., Nomura Chemical Co., Ltd., Japan) under the following conditions. As a mobile phase, (A) 0.08% formic acid and (B) 0.15% formic acid/80% acetonitrile were used. For the analysis, Agilent 1100 series HPLC system was used, and elution was carried out at a constant flow rate of 50 µl/min, firstly with the solution (A) for 5 minutes, then with gradient concentration of the solution (B) from 0% to 50% over 75 minutes. The eluate was introduced continuously into an electrospray ionization mass spectrometer (Esquire HCT, Bruker Daltonics GmbsH, Bremen, Germany).

a) Confirmation of Elution Positions of Peptides Present in the Test Samples:

In order to confirm elution positions where peptides and glycopeptides and the like present in the test samples obtained above, analysis of BPC (Base Peak Chromatography) was carried out.

Results are shown as BPC in FIG. 5A. It should be noted that the BPC in FIG. 5A indicates the peaks with the greatest intensity in both MS scan and MSMS scan repeated at intervals of 1.5 seconds.

b) Preliminary Identification of Elution Positions of the Glycopeptide Containing Site 2 and the Glycopeptide Containing Site 3:

In order to identify preliminarily elution positions of the glycopeptides containing Site 2 and Site 3, analysis of the following EIC (Extracted Ion Chromatogram) was carried out.

In the case of a complex-type oligosaccharide of Asn-type (carbohydrate compound having very complicated structure), since the Gal-GlcNAc (mass number: $[M+H]^+=366.3$ m/z) is susceptible to fragmentation in MSMS measurement, elution positions of the peptides having sugar chain can be identified by analyzing their mass numbers.

The EIC of MSMS (at m/z366.3) in FIG. 5A is a chromatogram indicating peak intensities of the fragment ion having a mass number of 366.3 m/z generated in the MSMS measurement of the test sample from normal volunteer (NV5).

As a result, peaks with high peak intensities were found at 5 and 52 minutes in the chromatogram.

c) Identification of Elution Positions of the Glycopeptides Containing Site 2:

In order to identify peak positions of the glycopeptides containing Site 2, intensities of the ion peak having a mass number ($[M+2H]^{2+}=1298.5$ m/z) of glycopeptide coupled with a biantennary N-glycan (asialo-biantennary N-glycan, derived by the removal of sialic acid) sugar chain (the sugar chain shown by 2-0 in the above-described FIG. 4) known as the principal carbohydrate structure of haptoglobin were analyzed.

The EIC of MS (at 1298.4-1299.4 m/z) Site 2 in FIG. 5A is a chromatogram showing peak intensities of the fragment ions having mass numbers of 1298.4-1299.4 m/z generated in the MS measurement of the test sample from normal volunteer (NV5).

As a result, elution position of the peak showing high intensity was found at around 52 minutes in the chromatogram. This was in good agreement with the elution position of 52 minutes obtained in the above described b) for the Gal-GlcNAc (mass number: $[M+H]^+=366.3$ m/z) derived from a complex type oligosaccharide of Asn-type in MSMS measurement.

From the results described above, the peak at around 52 minutes was identified as the peak assigned to the glycopeptide containing Site 2.

Though not shown in the figure, for both cases, where the test sample from a patient with pancreatic cancer (PC) was used and where the test sample from a patient with chronic pancreatitis (CP) was used, analyses were carried out in the same manner as described above, and the peak at around 52 minutes was identified as the peak assigned to the glycopeptides containing Site 2.

d) Identification of Elution Position of the Glycopeptides Containing Site 3:

In the same manner as described in the above c), in order to identify a peak position of the glycopeptides containing Site 3, intensities of the ion peak having a mass number ($[M+3H]^{3+}=1063.9$ m/z) of glycopeptide coupled with a biantennary N-glycan (asialo-biantennary N-glycan, derived by the removal of sialic acid) sugar chain (the sugar chain shown by 2-0 in the above-described FIG. 4) known as the principal carbohydrate structure of haptoglobin were analyzed.

The EIC of MS (at 1063.8-1064.8 m/z) Site 3 in FIG. 5A is a chromatogram showing peak intensities of the fragment ions having mass numbers of 1063.8-1064.8 m/z generated in the MS measurement of the test sample from normal volunteer (NV5).

As a result, an elution position of the peak showing high intensity was found at around 5 minutes in the chromatogram. This was in good agreement with the elution position of 5 minutes obtained in the above-described b) for the Gal-GlcNAc (mass number: $[M+H]^+=366.3$ m/z) derived from a complex type oligosaccharide of Asn-type in MSMS measurement.

From the results described above, the peak at around 5 minutes was identified as the peak assigned to the glycopeptide containing Site 3.

Though not shown in the figure, for both cases, where the test sample from a patient with pancreatic cancer (PC) was used and where the test sample from a patient with chronic pancreatitis (CP) was used, analyses were carried out in the same manner as described above, and the peak at around 5 minutes was identified as the peak assigned to the glycopeptides containing Site 3.

e) Determination of Carbohydrate Structure in Site 3 of Haptoglobin:

Averaging of the mass spectra around the elution positions (3-8 minutes) specified in the above-described d) for the glycopeptides containing Site 3 was carried out for each test sample from a normal volunteer (NV5), a patient with chronic pancreatitis (CP4) and a patient with pancreatic cancer (PC5).

Results are shown in FIG. 5B.

From the relationship between the mass numbers calculated as shown in FIG. 4 and the presumed various types of carbohydrate structures, and also from the mass number of the peak obtained for each test sample as shown in FIG. 5B, the carbohydrate structure of each peak was determined.

It should be noted that the first numeral put on the abbreviation of carbohydrate structure in FIG. 5B indicates number of branch; N and following numeral indicate number of NeuAc; and also F and following numeral indicate number of fucosylation.

In Table 3, the carbohydrate structures in Site 3 determined for each test sample from a normal volunteer (NV5), a patient with chronic pancreatitis (CP4) and a patient with pancreatic cancer (PC5) are shown.

TABLE 3

| Carbohydrate structure | Sample from normal volunteer | Sample from patient with chronic pancreatitis | Sample from patient with pancreatic cancer |
|---|---|---|---|
| 2-0 | ◯ | ◯ | ◯ |
| 2-F1 | ◯ | ◯ | ◯ |
| 3-0 | ◯ | ◯ | ◯ |
| 3-F1 | ◯ | ◯ | ◯ |
| 4-0 | ◯ | ◯ | ◯ |
| 4-F1 | ◯ | ◯ | ◯ |
| 4-F2 | X | X | ◯ | f) Determination of Carbohydrate Structure in Site 2 of Haptoglobin:

Averaging of the mass spectra near the elution positions (50-55 minutes) specified in the above-described c) for the glycopeptides containing Site 2 was carried out for each test sample from a normal volunteer (NV5), a patient with chronic pancreatitis (CP4) and a patient with pancreatic cancer (PC5) (It should be noted that the results of the mass spectra were not particularly shown), and then the carbohydrate structure of each peak was determined in the same manner as described in the above e).

In Table 4, the carbohydrate structures in Site 2 determined for each test sample from a normal volunteer (NV5), a patient with chronic pancreatitis (CP4) and a patient with pancreatic cancer (PC5) are shown.

TABLE 4

| Carbohydrate structure | Sample from normal volunteer | Sample from patient with chronic pancreatitis | Sample from patient with pancreatic cancer |
|---|---|---|---|
| 2-0 | ◯ | ◯ | ◯ |
| 2-F1 | ◯ | ◯ | ◯ |
| 3-0 | ◯ | ◯ | ◯ |
| 3-F1 | ◯ | ◯ | ◯ |
| 4-0 | X | X | X |
| 4-F1 | X | X | X |
| 4-F2 | X | X | X |

(3) Calculation of Relative Abundance of Various Types of Sugar Chains in Each Site of Haptoglobin:

Relative abundance of N-glycan (sugar chain) structure in Site 1 to Site 4 of haptoglobin was calculated based on the signal intensity of the corresponding glycopeptide obtained in the above-described LC-ESI MS analysis.

As to the Site 1 and the Site 4, each glycopeptide fragment was separated by the above-described LC-ESI MS depending on presence or absence of sialic acid and difference in its number. Therefore, in order to make them conformable with the results of the Site 2 and the Site 3, all of the carbohydrate structures (sialo-glycopeptides) determined in the above-described LC-ESI MS were divided into several groups so that the glycopeptides (sialo-glycopeptides) had an identical carbohydrate structure except for sialic acid, such as (1) a group which comprises unfucosylated biantennary (2-0) sugar chain (2-N1, 2-N2); (2) a group which comprises fucosylated biantennary (2-F1) sugar chain (2-N2-F1, 2-N2-F1); (3) a group which comprises unfucosylated triantennary (3-0) sugar chain (3-N2, 3-N3); (4) a group which comprises fucosylated triantennary (3-F1) sugar chain (3-N2-F1, 3-N3-F1); (5) a group which comprises unfucosylated tetraantennary (4-0) sugar chain (4-N1, 4-N2, 4-N3, 4-N4); and (6) a group which comprises fucosylated tetraantennary (4-F1) sugar chain (4-N1-F1, 4-N2-F1, 4-N3-F1, 4-N4-F1), for each individual sample. And then, the signal intensity (ion intensity) corresponding to each glycopeptide (sialo-glycopeptide) obtained in the above-described LS-ESI MS analysis was summed up in each group (as a summation).

Based on the summation of all signal intensity (ion intensity) of glycopeptides (sialo-glycopeptides) detected and identified for each test sample as 100%, a relative value (relative abundance (%)) of the summation (signal intensity (ion intensity)) of each group was calculated; and average values of 4 groups consisting of normal volunteers (NV) of age 40 or lower, normal volunteers (NV) of age 60 or over, patients with chronic pancreatitis (CP) and patients with pancreatic cancer (PC) were each calculated; and then these values were converted to a relative abundance (%) for each sugar chain with asialo-structure (2-0, 2-F1, 3-0, 3-F1, 4-0, 4-F1).

In addition, with respect to the Site 2 and the Site 3, since the above-described LC-ESI MS analyses were carried out using desialylated samples (desialylated glycopeptides), the signal intensities obtained were the one corresponding to the sugar chains with asialo-structure (asialo-glycopeptides) Therefore, using the value obtained in the above-described LC-ESI MS analysis as it was, and based on the summation of all signal intensities (ion intensities) of glycopeptides (sialo-glycopeptides) detected and identified for each test sample as 100%, the relative value (relative abundance (%)) of signal intensity (ion intensity) of each carbohydrate structure (asialo-glycopeptide) was calculated; and average values of 4 groups consisting of normal volunteers (NV) of age 40 or lower, normal volunteers (NV) of age 60 or over, patients with chronic pancreatitis (CP) and patients with pancreatic cancer (PC) were each calculated; and then these values were converted to relative abundance (%) for each sugar chain with asialo-structure (2-0, 2-F1, 3-0, 3-F1, 4-0, 4-F1, 4-F2).

Relative abundances of the sugar chains with asialo-structure in each Site are shown in Table 5 to Table 8.

TABLE 5

| | Sugar chain with asialo-structure (Sugar chain with sialo-structure) | Normal volunteer NV(<40) (%) | Normal volunteer NV(>60) (%) | Patient with Chronic pancreatitis CP (%) | Patient with pancreatic cancer PC (%) |
|---|---|---|---|---|---|
| Site 1 | 2-0 | 68.0 | 67.5 | 74.9 | 70.8 |
| | (2-N1 + 2-N2) | (10.7 + 57.3) | (13.6 + 53.9) | (15.9 + 59.0) | (9.9 + 60.9) |
| | 3.0 | 26.8 | 25.4 | 17.7 | 15.4 |
| | (3-N2 + 3-N3) | (5.3 + 21.5) | (5.5 + 19.9) | (4.6 + 13.1) | (2.9 + 12.5) |
| | 4-0 | 0.0 | 0.0 | 0.0 | 0.0 |
| | (4-N1 + 4-N2 + 4-N3 + 4-N4) | (0.0 + 0.0 + 0.0 + 0.0) | (0.0 + 0.0 + 0.0 + 0.0) | (0.0 + 0.0 + 0.0 + 0.0) | (0.0 + 0.0 + 0.0 + 0.0) |
| | 2-F1 | 1.9 | 2.6 | 3.8 | 3.4 |
| | (2-N1-F1 + 2-N2-F1) | (0.1 + 1.8) | (0.3 + 2.3) | (1.1 + 2.7) | (0.5 + 2.9) |
| | 3-F1 | 3.3 | 4.5 | 3.6 | 10.5 |
| | (3-N2-F1 + 3-N3-F1) | (0.4 + 2.9) | (0.7 + 3.8) | (0.5 + 3.1) | (1.2 + 9.3) |
| | 4-F1 | 0.0 | 0.0 | 0.0 | 0.0 |
| | (4-N1-F1 + 4-N2-F1 + 4-N3-F1 + 4-N4-F1) | (0.0 + 0.0 + 0.0 + 0.0) | (0.0 + 0.0 + 0.0 + 0.0) | (0.0 + 0.0 + 0.0 + 0.0) | (0.0 + 0.0 + 0.0 + 0.0) |

TABLE 6

| | Sugar chain with asialo-structure | Normal volunteer NV(<40) (%) | Normal volunteer NV(>60) (%) | Patient with chronic pancreatitis CP (%) | Patient with pancreatic cancer PC (%) |
|---|---|---|---|---|---|
| Site 2 | 2-0 | 72.8 | 70.1 | 68.1 | 72.9 |
| | 3.0 | 22.5 | 22.2 | 23.3 | 14.5 |
| | 4-0 | 0.0 | 0.0 | 0.0 | 0.0 |
| | 2-F1 | 2.6 | 4.2 | 4.3 | 6.7 |
| | 3-F1 | 2.1 | 3.5 | 4.3 | 5.9 |
| | 4-F1 | 0.0 | 0.0 | 0.0 | 0.0 |
| | 4-F2 | 0.0 | 0.0 | 0.0 | 0.0 |

TABLE 7

| | Sugar chain with asialo-structure | Normal volunteer NV(<40) (%) | Normal volunteer NV(>60) (%) | Patient with chronic pancreatitis CP (%) | Patient with pancreatic cancer PC (%) |
|---|---|---|---|---|---|
| Site 3 | 2-0 | 31.2 | 31.9 | 30.1 | 29.2 |
| | 3.0 | 42.8 | 37.2 | 39.3 | 26.1 |
| | 4-0 | 9.6 | 10.8 | 9.0 | 9.2 |
| | 2-F1 | 3.6 | 3.0 | 4.8 | 4.5 |
| | 3-F1 | 9.1 | 14.3 | 13.1 | 19.6 |
| | 4-F1 | 3.8 | 2.7 | 3.8 | 8.1 |
| | 4-F2 | 0.0 | 0.0 | 0.0 | 3.2 |

TABLE 8

| Sugar chain with asialo-structure (Sugar chain with sialo-structure) | Normal volunteer NV(<40) (%) | Normal volunteer NV(>60) (%) | Patient with chronic pancreatitis CP (%) | Patient with pancreatic cancer PC (%) |
|---|---|---|---|---|
| Site 4 | 2-0 | 75.3 | 76.2 | 77.6 | 72.7 |
| | (2-N1 + 2-N2) | (2.7 + 72.6) | (7.1 + 69.1) | (4.6 + 73.0) | (2.9 + 69.8) |
| | 3-0 | 17.6 | 15.5 | 14.3 | 14.9 |
| | (3-N2 + 3-N3) | (5.8 + 11.8) | (6.2 + 9.3) | (5.7 + 8.6) | (6.0 + 8.9) |
| | 4-0 | 3.3 | 4.0 | 2.5 | 2.7 |
| | (4-N1 + 4-N2 + 4-N3 + 4-N4) | (0.4 + 1.1 + 1.2 + 0.6) | (0.0 + 1.3 + 2.0 + 0.7) | (0.5 + 0.7 + 0.9 + 0.4) | (0.3 + 0.9 + 1.0 + 0.5) |
| | 2-F1 | 1.0 | 1.4 | 1.8 | 2.8 |
| | (2-N1-F1 + 2-N2-F1) | (0.2 + 0.8) | (0.3 + 1.1) | (0.2 + 1.4) | (0.4 + 2.4) |
| | 3-F1 | 2.4 | 1.6 | 3.3 | 5.7 |
| | (3-N2-F1 + 3-N3-F1) | (0.3 + 2.1) | (0.0 + 1.6) | (0.6 + 2.7) | (1.1 + 4.6) |
| | 4-F1 | 0.4 | 1.3 | 0.7 | 1.2 |
| | (4-N1-F1 + 4-N2-F1 + 4-N3-F1 + 4-N4-F1) | (0.09 + 0.17 + 0.05 + 0.09) | (0.6 + 0.4 + 0.0 + 0.3) | (0.11 + 0.19 + 0.27 + 0.13) | (0.2 + 0.3 + 0.4 + 0.3) |

In addition, the relationships between the relative abundance of sugar chain with asialo-structure in each Site and each test sample are shown in FIG. 6.

It should be noted that significance test of the relative abundance was studied at first by multiple comparison of carbohydrate structure of each Site among 4 groups by non-repeated measured ANOVA, then only for the carbohydrate structures for which significant difference was observed, each pair of 2 groups among 4 groups was compared using Bonferroni's correction.

(4) Calculation of Relative Abundance of Fucosylated Sugar Chain and Unfucosylated Sugar Chain in Each Site of Haptoglobin:

In each Site, relative abundance (%) concerning fucosylated sugar chain and the relative abundance (%) concerning unfucosylated sugar chain were calculated.

That is, in the same manner as described in the above (3), as to the Site 1 and the Site 4, all of the carbohydrate structures (sialo-glycopeptides) determined in the above-described LC-ESI MS was divided into 2 groups, comprising (1) the one which did not have fucosylated sugar chain [unfucosylated sugar chain (without Fuc)] (2-N1, 2-N2, 3-N2, 3-N3, 4-N1, 4-N2, 4-N3, 4-N4) and (2) the one which had fucosylated sugar chain (with Fuc) (2-N1-F1, 2-N2-F1, 3-N2-F1, 3-N3-F1, 4-N1-F1, 4-N2-F1, 4-N3-F1, 4-N4-F1), for each individual test sample. And then, the signal intensity (ion intensity) corresponding to each glycopeptide (sialo-glycopeptide) obtained in the above-described LS-ESI MS analysis was summed up in each group (as a summation).

Based on the summation of all signal intensities (ion intensities) of glycopeptides (sialo-glycopeptides) detected and identified for each test sample as 100%, a relative value (relative abundance (%)) of the summation (signal intensity (ion intensity)) of each group was calculated; and average values of 4 groups consisting of normal volunteers (NV) of age 40 or lower, normal volunteers (NV) of age 60 or over, patients with chronic pancreatitis (CP) and patients with pancreatic cancer (PC) were each calculated; and then a relative abundance (%) of fucosylated sugar chain and a relative abundance (%) of unfucosylated sugar chain were calculated.

In addition, as to the Site 2 and the Site 3, in the same manner as described above, all of the carbohydrate structures (asialo-glycopeptides) determined in the above-described LC-ESI MS were divided into 2 groups, comprising (1) the one which did not have fucosylated sugar chain [unfucosylated sugar chain (without Fuc)] (2-0, 3-0, 3-N2, 4-0) and (2) the one which had fucosylated sugar chain (with Fuc) (2-F1, 3-F1, 4-F1, 4-F2), for each individual test sample. And then, the signal intensities (ion intensities) corresponding to each glycopeptide (asialo-glycopeptide) obtained in the above-described LS-ESI MS analysis were summed up in each group (as a summation).

Based on the summation of all signal intensities (ion intensities) of glycopeptides (asialo-glycopeptides) detected and identified for each test sample as 100%, a relative value (relative abundance (%)) of the summation (signal intensity (ion intensity)) of each group was calculated; and average values of 4 groups consisting of normal volunteers (NV) of age 40 or lower, normal volunteers (NV) of age 60 or over, patients with chronic pancreatitis (CP) and patients with pancreatic cancer (PC) were each calculated; and then a relative abundance (%) of fucosylated sugar chain and a relative abundance (%) of unfucosylated sugar chain were calculated.

In Table 9 to Table 12, relative abundances of fucosylated sugar chain and relative abundances of unfucosylated sugar chain in each Site are shown.

TABLE 9

| | | Normal volunteer NV(<40) (%) | Normal volunteer NV(>60) (%) | Patient with chronic pancreatitis CP (%) | Patient with pancreatic cancer PC (%) |
|---|---|---|---|---|---|
| Site 1 | Unfucosylated sugar chain (2-N1 + 2-N2 + 3-N2 + 3-N3 + 4-N1 + 4-N2 + 4-N3 + 4-N4) | 94.8 | 92.9 | 92.6 | 86.1 |
| | Fucosylated sugar chain (2-N1-F1 + 2-N2-F1 + 3-N2-F1 + 3-N3-F1 + 4-N1-F1 + 4-N2-F1 + 4-N3-F1 + 4-N4-F1 + 4-F2) | 5.2 | 7.1 | 7.4 | 13.9 |

TABLE 10

|  |  | Normal volunteer NV(<40) (%) | Normal volunteer NV(>60) (%) | Patient with chronic pancreatitis CP (%) | Patient with pancreatic cancer PC (%) |
|---|---|---|---|---|---|
| Site 2 | Unfucosylated sugar chain (2-0 + 3-0 + 4-0) | 95.3 | 92.3 | 91.4 | 87.4 |
|  | Fucosylated sugar chain (2-F1 + 3-F1 + 4-F1 + 4-F2) | 4.7 | 7.7 | 8.6 | 12.6 |

TABLE 11

|  |  | Normal volunteer NV(<40) (%) | Normal volunteer NV(>60) (%) | Patient with chronic pancreatitis CP (%) | Patient with pancreatic cancer PC (%) |
|---|---|---|---|---|---|
| Site 3 | Unfucosylated sugar chain (2-0 + 3-0 + 4-0) | 83.6 | 79.9 | 78.4 | 64.6 |
|  | Fucosylated sugar chain (2-F1 + 3-F1 + 4-F1 + 4-F2) | 16.4 | 20.1 | 21.6 | 35.4 |

TABLE 12

|  |  | Normal volunteer NV(<40) (%) | Normal volunteer NV(>60) (%) | Patient with chronic pancreatitis CP (%) | Patient with pancreatic cancer PC (%) |
|---|---|---|---|---|---|
| Site 4 | Unfucosylated sugar chain (2-N1 + 2-N2 + 3-N2 + 3-N3 + 4-N1 + 4-N2 + 4-N3 + 4-N4) | 96.2 | 95.7 | 94.4 | 90.4 |
|  | Fucosylated sugar chain (2-N1-F1 + 2-N2-F1 + 3-N2-F1 + 3-N3-F1 + 4-N1-F1 + 4-N2-F1 + 4-N3-F1 + 4-N4-F1 + 4-F2) | 3.8 | 4.3 | 5.6 | 9.6 |

In addition, the relationships between the relative abundance of fucosylated sugar chain and the relative abundance of unfucosylated sugar chain in each Site and each test sample are shown in FIG. 7.

It should be noted that significance test of the relative abundance was studied firstly by multiple comparison of carbohydrate structure of each Site among 4 groups by non-repeated measured ANOVA, then only for the carbohydrate structures for which significant difference was observed, every pair of 2 groups among 4 groups was compared using Bonferroni's correction.

(5) Results:

From the results shown in Table 5 to 8 and FIG. 6, it can be understood that, in the Site 1, the carbohydrate structure of 3-F1 (corresponding to the tumor marker for pancreatic cancer [II] and [2] of the present invention) is significantly increased in the patients with pancreatic cancer compared with those of the other groups (normal volunteers and patients with chronic pancreatitis), and also in the Site 3, the carbohydrate structure of 3-F1 (corresponding to the tumor marker for pancreatic cancer [II] and [2] of the present invention) and 4-F1 [corresponding to the tumor marker for pancreatic cancer [III] of the present invention and the tumor marker for pancreatic cancer [3] of the present invention comprising the fucosylated sugar chain containing the carbohydrate structure (sequence) shown by the above-described structural formula [III], wherein any one of N-acetylglucosamine (GlcNAc) in the tetraantennary sugar chain present in the non-reducing terminal side is fucosylated] is significantly increased in the patients with pancreatic cancer compared with those of the other groups (normal volunteers and patients with chronic pancreatitis). Further, it can be understood that the carbohydrate structure of 4-F1 in the Site 3 is not found in the other Sites except that slightly found in Site 4, and that the carbohydrate structure of 4-F2 [corresponding to the tumor marker for pancreatic cancer [III] of the present invention and the tumor marker for pancreatic cancer [4] of the present invention comprising the fucosylated sugar chain containing the carbohydrate structure (sequence) shown by the above described structural formula [III], wherein at least 2 sites which include any one of N-acetylglucosamine (GlcNAc) in the tetraantennary sugar chain present in the non-reducing terminal side and any one of galactose (Gal) in the tetraantennary sugar chain present in the non-reducing terminal side were fucosylated] in the Site 3 is found only in the patients with pancreatic cancer.

From the results described above, it is suggested that the amount of the tumor marker for pancreatic cancer of the present invention as described above in the Site 1 and/or the Site 3 is useful as a marker (or an indicator) for determining (diagnosing, testing) pancreatic cancer.

In addition, from the results shown in Tables 9 to 12 and FIG. 7, it can be understood that, while an increase in the relative abundance of the fucosylated sugar chain is observed in either Site in the patients with pancreatic cancer, particularly, an increase of the fucosylated sugar chain [corresponding to the total amount of the tumor markers for pancreatic cancer [I] to [III] of the present invention and the total amount of the tumor marker for pancreatic cancer [1] to [4] of the present invention] in Site 1 or Site 3 is significantly great compared with those of the other Sites. In addition, it can be understood that, in the Site 1 and the Site 3, the fucosylated sugar chain from patients with pancreatic cancer is increased significantly compared with those from the other groups (normal volunteers and patients with chronic pancreatitis).

From the foregoing, it is suggested that the amount of the fucosylated sugar chain in the Site 1 and/or the Site 3 in human haptoglobin is useful as a marker (or an indicator) for determining (diagnosing, testing) pancreatic cancer.

The method of determination using a tumor marker for pancreatic cancer of the present invention enables to perform the determination (diagnosis, test) of pancreatic cancer with higher accuracy. In addition, since the tumor marker for pancreatic cancer of the present invention can be found, for example, in the serum, the determination (diagnosis, test) of pancreatic cancer can be performed noninvasively and easily.

What is claimed is:

1. A method of determining pancreatic cancer, comprising measuring an amount of a fucosylated sugar chain bound to asparagine at position 184, position 211, or positions 184 and 211 from the N-terminus of the amino acid sequence of human haptoglobin present in a biological sample or a relative value of the amount of the fucosylated sugar chain to a total amount of all sugar chain bound to the same asparagines present in the biological sample, and determining pancreatic cancer by using the amount of the fucosylated sugar chain or the relative value of the amount of the fucosylated sugar chain, as a marker for the determination of pancreatic cancer.

2. The method according to claim 1, wherein the sugar chain of the fucosylated sugar chain comprises at least one of the carbohydrate structures shown by the following structural formulas [I]-[III]:

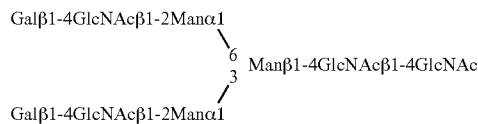

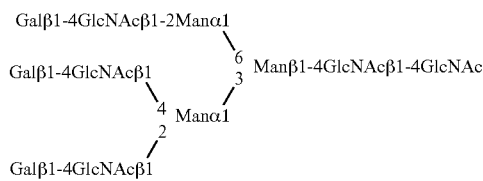

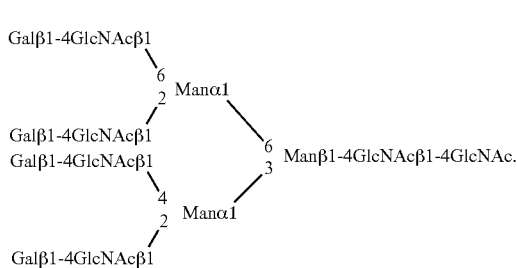

3. The method according to claim 1, wherein the sugar chain of the fucosylated sugar chain is bound to asparagine at position 184 from the N-terminus of the amino acid sequence of human haptoglobin, and comprises the carbohydrate structure shown by the following structural formula [II]:

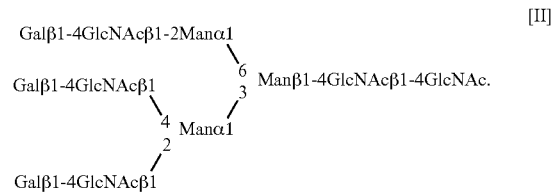

4. The method according to claim 1, wherein the sugar chain of the fucosylated sugar chain is bound to asparagine at position 211 from the N-terminus of the amino acid sequence of human haptoglobin, and comprises at least one of the carbohydrate structures shown by the following structural formulas [II]-[III]:

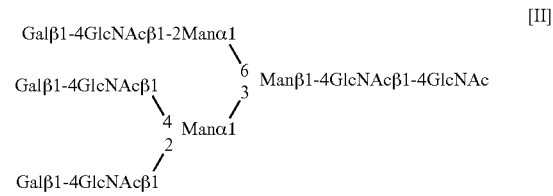

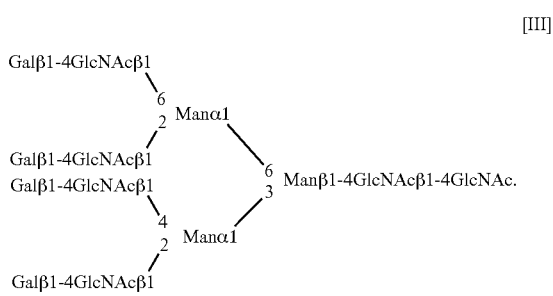

5. The method according to claim 1, wherein the sugar chain of the fucosylated sugar chain is bound to asparagine at position 211 from the N-terminus of the amino acid sequence of human haptoglobin, and comprises the carbohydrate structure shown by the following structural formula [III]:

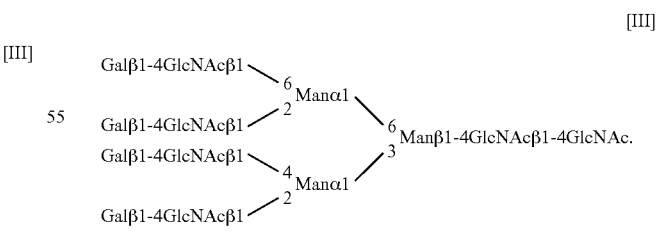

6. A tumor marker for pancreatic cancer, comprising a carbohydrate structure present in human haptoglobin and shown by the following structural formula [III], wherein at least one of N-acetylglucosamine (GlcNAc) in the tetraantennary sugar chain shown by Galβ1-4GlcNAcβ1- in the following structural formula [III] is fucosylated:

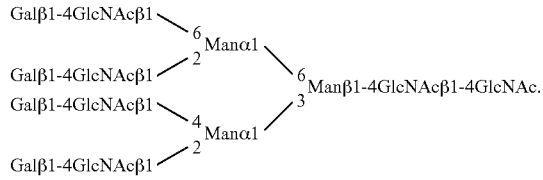

[III]

7. The tumor marker for pancreatic cancer according to claim 6, wherein the carbohydrate structure comprises the carbohydrate structure shown by the following structural formula [III], and at least one of N-acetylglucosamine (GlcNAc) in the tetraantennary sugar chain shown by Galβ1-4GlcNAcβ1- in the following structural formula [III] and at least one of galactose (Gal) in the tetraantennary sugar chain shown by Galβ1-4GlcNAcβ1- in the following structural formula [III] are fucosylated:

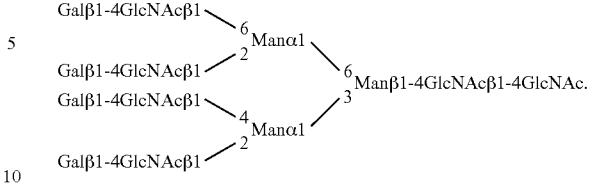

[III]

8. The tumor marker for pancreatic cancer according to claim 6, wherein the carbohydrate structure is bound to asparagine at position 211 from the N-terminus of amino acid sequence of human haptoglobin.

9. A method of determining pancreatic cancer, comprising measuring an amount of the tumor marker for pancreatic cancer according to claim 6 present in a biological sample, and determining pancreatic cancer by using the amount of the tumor marker for pancreatic cancer, as a marker for the determination of pancreatic cancer.

\* \* \* \* \*